(12) United States Patent
Poltaretskyi et al.

(10) Patent No.: US 12,042,234 B2
(45) Date of Patent: Jul. 23, 2024

(54) TRACKING SURGICAL PIN

(71) Applicant: Howmedica Osteonics Corp., Mahwah, NJ (US)

(72) Inventors: Sergii Poltaretskyi, Ependes FR (CH); Nicolas Neichel, Le Sappey en Chartreuse (FR)

(73) Assignee: Howmedica Osteonics Corp., Mahwah, NJ (US)

( * ) Notice: Subject to any disclaimer, the term of this patent is extended or adjusted under 35 U.S.C. 154(b) by 134 days.

(21) Appl. No.: 17/771,415

(22) PCT Filed: Nov. 20, 2020

(86) PCT No.: PCT/US2020/061598
§ 371 (c)(1),
(2) Date: Apr. 22, 2022

(87) PCT Pub. No.: WO2021/108265
PCT Pub. Date: Jun. 3, 2021

(65) Prior Publication Data
US 2022/0361960 A1   Nov. 17, 2022

Related U.S. Application Data

(60) Provisional application No. 62/940,819, filed on Nov. 26, 2019, provisional application No. 62/940,826, filed on Nov. 26, 2019.

(51) Int. Cl.
A61B 34/20    (2016.01)
A61B 17/17    (2006.01)
(Continued)

(52) U.S. Cl.
CPC .......... *A61B 34/25* (2016.02); *A61B 17/1703* (2013.01); *A61B 17/848* (2013.01); *A61B 34/20* (2016.02); *A61B 90/39* (2016.02); *G02B 27/0172* (2013.01); *G16H 20/40* (2018.01); *A61B 2034/105* (2016.02); *A61B 2034/107* (2016.02); *A61B 2034/2055* (2016.02); *A61B 2034/2065* (2016.02);
(Continued)

(58) Field of Classification Search
CPC .... A61B 2034/2055; A61B 2090/3937; A61B 90/90–96
See application file for complete search history.

(56) References Cited

U.S. PATENT DOCUMENTS

| 10,278,726 | B2 | 5/2019 | Barth et al. |
| 2014/0058257 | A1 | 2/2014 | Stigall et al. |
| 2019/0000405 | A1 | 1/2019 | Shoup et al. |

FOREIGN PATENT DOCUMENTS

| EP | 3533409 A1 | 9/2019 |
| WO | 2008038282 A2 | 4/2008 |
| WO | 2014159913 A1 | 10/2014 |

OTHER PUBLICATIONS

International Preliminary Report on Patentability from International Application No. PCT/US2020/061598, dated Jun. 9, 2022, 13 pp.
(Continued)

*Primary Examiner* — Colin T. Sakamoto
(74) *Attorney, Agent, or Firm* — Shumaker & Sieffert, P.A.

(57) ABSTRACT

An example surgical pin configured to be installed in a bone of a patient includes a distal end; a shaft comprising a plurality of longitudinally spaced visually marked regions separated by non-marked regions; and a proximal end.

4 Claims, 15 Drawing Sheets

(51) Int. Cl.
*A61B 17/84* (2006.01)
*A61B 34/00* (2016.01)
*A61B 90/00* (2016.01)
*G02B 27/01* (2006.01)
*G16H 20/40* (2018.01)
*A61B 34/10* (2016.01)
*A61B 90/50* (2016.01)

(52) U.S. Cl.
CPC ... *A61B 2034/252* (2016.02); *A61B 2090/372* (2016.02); *A61B 2090/3937* (2016.02); *A61B 2090/502* (2016.02); *G02B 2027/0138* (2013.01); *G02B 2027/014* (2013.01); *G02B 2027/0141* (2013.01)

(56) References Cited

OTHER PUBLICATIONS

International Search Report and Written Opinion of International Application No. PCT/US2020/061598, dated Apr. 7, 2021, 21 pp.
Invitation to Pay Additional Fees and, Where Applicable, Protest Fee from International Application No. PCT/US2020/061598, dated Feb. 18, 2021, 14 pp.

TRACKING SURGICAL PIN

This application is a national stage application under 35 U.S.C. § 371 of PCT Application No. PCT/US2020/061598, filed Nov. 20, 2020, which claims the benefit of U.S. Provisional Application No. 62/940,819, filed Nov. 26, 2019, and U.S. Provisional Application No. 62/940,826, filed Nov. 26, 2019. The entire contents of each of PCT Application No. PCT/US2020/061598, U.S. Provisional Application No. 62/940,819, and U.S. Provisional Application No. 62/940,826 are incorporated herein by reference in their entirety.

BACKGROUND

Surgical joint repair procedures involve repair and/or replacement of a damaged or diseased joint. Many times, a surgical joint repair procedure, such as joint arthroplasty as an example, involves replacing the damaged joint with a prosthetic, or set of prosthetics, that is implanted into the patient's bone. To assist with positioning, the surgical procedure often involves the use of surgical instruments to control the shaping of the surface of the damaged bone and cutting or drilling of bone to accept the prosthetic. The use of some surgical instruments (e.g., cannulated instruments) involves the use of surgical pins installed into bone.

SUMMARY

In some orthopedic surgical procedures, a surgeon may implant one or more implant devices in a patient. The surgeon may perform various surgical steps to prepare the patient's bone to receive the implant device. These surgical steps may include insertion of guide pins, modifications to a surface of the bone (e.g., via reaming), removal of portions of the bone (e.g., resection), creating anchorage points, or other surgical steps.

A visualization device may display virtual guidance that assists a surgeon in performing one or more of the surgical steps to prepare the patient's bone to receive the implant device. For instance, the visualization device may display a virtual axis to indicate a physical axis along which the surgeon is to install a surgical pin in a bone of a patient. The virtual axis may correspond to a planned orientation and a planned position of the surgical pin. The surgeon may achieve correct performance of the surgical step by aligning a shaft of the surgical pin with the displayed virtual axis, activating a driver of the surgical pin, and advancing the shaft of the surgical pin along the displayed virtual axis. However, in some scenarios, a surgeon may not install a surgical pin correctly. For instance, due to various issues, the surgeon may install the pin at an incorrect orientation.

In accordance with one or more techniques of this disclosure, a visualization device may provide virtual guidance to assist a surgeon in correcting the installation of a surgical pin. For instance, after initial installation of a surgical pin into a bone of a patient, the visualization device may determine whether an actual orientation of the surgical pin (e.g., as installed) matches a planned orientation of the surgical pin. If the actual orientation does not match the planned orientation, the visualization device may output virtual guidance to assist a surgeon in correcting the installation of a surgical pin.

In some scenarios, it may be difficult for the visualization device to be able to determine the actual orientation of a traditional surgical pin. For instance, where the visualization device is worn on a head of the surgeon who is looking down at a surgical field, it may be difficult to determine the orientation of a surgical pin in the surgical field where the surgical pin is a solid piece of metal.

In accordance with one or more techniques of this disclosure, a surgical pin may include one or more visually marked regions configured to facilitate detection of the surgical pin. For instance, a surgical pin may include two etched or otherwise visually differentiated regions along a main body. A visualization device may utilize the visually marked regions to determine an orientation and/or a position of the surgical pin. For instance, the visualization device may utilize one or more cameras to capture an image of the surgical field that includes the surgical pin. The visualization device may analyze the image to identify end points of each of the one or more visually marked regions, and determine a three-dimensional (3D) location of each end point. Based on the 3D locations of the end points, the visualization device may determine the orientation and/or the position of the surgical pin. In this way, the techniques of this disclosure enable automated identification of surgical pins.

The details of various examples of the disclosure are set forth in the accompanying drawings and the description below. Various features, objects, and advantages will be apparent from the description, drawings, and claims.

DETAILED DESCRIPTION

Figure 1:
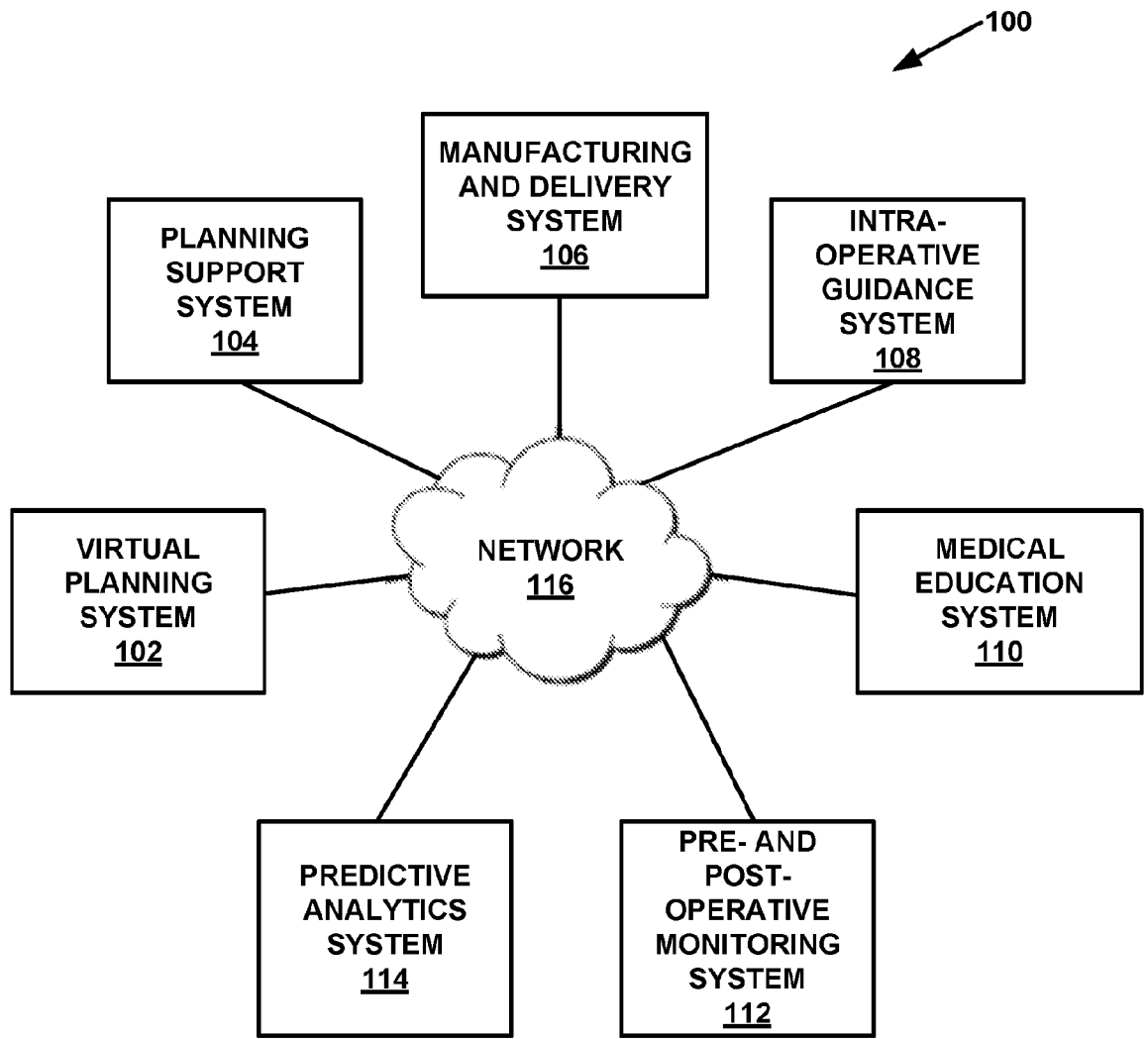
FIG. 1 is a block diagram of an orthopedic surgical system according to an example of this disclosure.

Orthopedic surgery can involve implanting one or more implant devices to repair or replace a patient's damaged or diseased joint. Virtual surgical planning tools that use image data of the diseased or damaged joint may be used to generate an accurate three-dimensional bone model that can be viewed and manipulated preoperatively by the surgeon. These tools can enhance surgical outcomes by allowing the surgeon to simulate the surgery, select or design an implant that more closely matches the contours of the patient's actual bone, and select or design surgical instruments and guide tools that are adapted specifically for repairing the bone of a particular patient. Use of these planning tools typically results in generation of a preoperative surgical plan, complete with an implant and surgical instruments that are selected or manufactured for the individual patient.

A surgeon may want to view details of the preoperative surgical plan relative to the patient's real bone during the actual procedure in order to more efficiently and accurately position and orient the implant components. For example, the surgeon may want to obtain intraoperative visualization that provides guidance for positioning and orientation of implant components, guidance for preparation of bone or tissue to receive the implant components, guidance for reviewing the details of a procedure or procedural step, and/or guidance for selection of tools or implants and tracking of surgical procedure workflow.

Accordingly, this disclosure describes systems and methods for using a mixed reality (MR) visualization system to assist with creation, implementation, verification, and/or modification of a surgical plan before and during a surgical procedure. Because MR may be used to interact with the surgical plan, this disclosure may also refer to the surgical plan as a "virtual" surgical plan. Visualization tools other than or in addition to mixed reality visualization systems may be used in accordance with techniques of this disclosure. A surgical plan, e.g., as generated by the BLUE-PRINT™ system, available from Wright Medical Group, N.V., or another surgical planning platform, may include information defining a variety of features of a surgical procedure, such as features of particular surgical procedure steps to be performed on a patient by a surgeon according to the surgical plan including, for example, bone or tissue preparation steps and/or steps for selection, modification and/or placement of implant components. Such information may include, in various examples, dimensions, shapes, angles, surface contours, and/or orientations of implant components to be selected or modified by surgeons, dimensions, shapes, angles, surface contours and/or orientations to be defined in bone or tissue by the surgeon in bone or tissue preparation steps, and/or positions, axes, planes, angle and/or entry points defining placement of implant components by the surgeon relative to patient bone or tissue. Information such as dimensions, shapes, angles, surface contours, and/or orientations of anatomical features of the patient may be derived from imaging (e.g., x-ray, CT, MRI, ultrasound or other images), direct observation, or other techniques.

In this disclosure, the term "mixed reality" (MR) refers to the presentation of virtual objects such that a user sees images that include both real, physical objects and virtual objects. Virtual objects may include text, 2-dimensional surfaces, 3-dimensional models, or other user-perceptible elements that are not actually present in the physical, real-world environment in which they are presented as coexisting. In addition, virtual objects described in various examples of this disclosure may include graphics, images, animations or videos, e.g., presented as 3D virtual objects or 2D virtual objects. Virtual objects may also be referred to as virtual elements. Such elements may or may not be analogs of real-world objects. In some examples, in mixed reality, a camera may capture images of the real world and modify the images to present virtual objects in the context of the real world. In such examples, the modified images may be displayed on a screen, which may be head-mounted, hand-held, or otherwise viewable by a user. This type of mixed reality is increasingly common on smartphones, such as where a user can point a smartphone's camera at a sign written in a foreign language and see in the smartphone's screen a translation in the user's own language of the sign superimposed on the sign along with the rest of the scene captured by the camera. In some examples, in mixed reality, see-through (e.g., transparent) holographic lenses, which may be referred to as waveguides, may permit the user to view real-world objects, i.e., actual objects in a real-world environment, such as real anatomy, through the holographic lenses and also concurrently view virtual objects.

The Microsoft HOLOLENS™ headset, available from Microsoft Corporation of Redmond, Washington, is an example of a MR device that includes see-through holographic lenses, sometimes referred to as waveguides, that permit a user to view real-world objects through the lens and concurrently view projected 3D holographic objects. The Microsoft HOLOLENS™ headset, or similar waveguide-based visualization devices, are examples of an MR visualization device that may be used in accordance with some examples of this disclosure. Some holographic lenses may present holographic objects with some degree of transparency through see-through holographic lenses so that the user views real-world objects and virtual, holographic objects. In some examples, some holographic lenses may, at times, completely prevent the user from viewing real-world objects and instead may allow the user to view entirely virtual environments. The term mixed reality may also encompass scenarios where one or more users are able to perceive one or more virtual objects generated by holographic projection. In other words, "mixed reality" may encompass the case where a holographic projector generates holograms of elements that appear to a user to be present in the user's actual physical environment.

In some examples, in mixed reality, the positions of some or all presented virtual objects are related to positions of physical objects in the real world. For example, a virtual object may be tethered to a table in the real world, such that the user can see the virtual object when the user looks in the direction of the table but does not see the virtual object when the table is not in the user's field of view. In some examples, in mixed reality, the positions of some or all presented virtual objects are unrelated to positions of physical objects in the real world. For instance, a virtual item may always appear in the top right of the user's field of vision, regardless of where the user is looking.

Augmented reality (AR) is similar to MR in the presentation of both real-world and virtual elements, but AR generally refers to presentations that are mostly real, with a few virtual additions to "augment" the real-world presentation. For purposes of this disclosure, MR is considered to include AR. For example, in AR, parts of the user's physical environment that are in shadow can be selectively brightened without brightening other areas of the user's physical environment. This example is also an instance of MR in that the selectively-brightened areas may be considered virtual objects superimposed on the parts of the user's physical environment that are in shadow.

Furthermore, in this disclosure, the term "virtual reality" (VR) refers to an immersive artificial environment that a user experiences through sensory stimuli (such as sights and sounds) provided by a computer. Thus, in virtual reality, the user may not see any physical objects as they exist in the real world. Video games set in imaginary worlds are a common example of VR. The term "VR" also encompasses scenarios where the user is presented with a fully artificial environment in which some virtual object's locations are based on the locations of corresponding physical objects as they relate to the user. Walk-through VR attractions are examples of this type of VR.

The term "extended reality" (XR) is a term that encompasses a spectrum of user experiences that includes virtual reality, mixed reality, augmented reality, and other user experiences that involve the presentation of at least some perceptible elements as existing in the user's environment that are not present in the user's real-world environment. Thus, the term "extended reality" may be considered a genus for MR and VR. XR visualizations may be presented in any of the techniques for presenting mixed reality discussed elsewhere in this disclosure or presented using techniques for presenting VR, such as VR goggles.

Visualization tools may utilize patient image data to generate three-dimensional models of bone contours to facilitate preoperative planning for joint repairs and replacements. These tools allow surgeons to design and/or select surgical guides and implant components that closely match the patient's anatomy. These tools can improve surgical outcomes by customizing a surgical plan for each patient. An example of such a visualization tool for shoulder repairs is the BLUEPRINT™ system available from Wright Medical Group, N.V. The BLUEPRINT™ system provides the surgeon with two-dimensional planar views of the bone repair region as well as a three-dimensional virtual model of the repair region. The surgeon can use the BLUEPRINT™ system to select, design or modify appropriate implant components, determine how best to position and orient the implant components and how to shape the surface of the bone to receive the components, and design, select or modify surgical guide tool(s) or instruments to carry out the surgical plan. The information generated by the BLUEPRINT™ system is compiled in a preoperative surgical plan for the patient that is stored in a database at an appropriate location (e.g., on a server in a wide area network, a local area network, or a global network) where it can be accessed by the surgeon or other care provider, including before and during the actual surgery.

FIG. 1 is a block diagram of an orthopedic surgical system 100 according to an example of this disclosure. Orthopedic surgical system 100 includes a set of subsystems. In the example of FIG. 1, the subsystems include a virtual planning system 102, a planning support system 104, a manufacturing and delivery system 106, an intraoperative guidance system 108, a medical education system 110, a monitoring system 112, a predictive analytics system 114, and a communications network 116. In other examples, orthopedic surgical system 100 may include more, fewer, or different subsystems. For example, orthopedic surgical system 100 may omit medical education system 110, monitoring system 112, predictive analytics system 114, and/or other subsystems. In some examples, orthopedic surgical system 100 may be used for surgical tracking, in which case orthopedic surgical system 100 may be referred to as a surgical tracking system. In other cases, orthopedic surgical system 100 may be generally referred to as a medical device system.

Users of orthopedic surgical system 100 may use virtual planning system 102 to plan orthopedic surgeries. Users of orthopedic surgical system 100 may use planning support system 104 to review surgical plans generated using orthopedic surgical system 100. Manufacturing and delivery system 106 may assist with the manufacture and delivery of items needed to perform orthopedic surgeries. Intraoperative guidance system 108 provides guidance to assist users of orthopedic surgical system 100 in performing orthopedic surgeries. Medical education system 110 may assist with the education of users, such as healthcare professionals, patients, and other types of individuals. Pre- and postoperative monitoring system 112 may assist with monitoring patients before and after the patients undergo surgery. Predictive analytics system 114 may assist healthcare professionals with various types of predictions. For example, predictive analytics system 114 may apply artificial intelligence techniques to determine a classification of a condition of an orthopedic joint, e.g., a diagnosis, determine which type of surgery to perform on a patient and/or which type of implant to be used in the procedure, determine types of items that may be needed during the surgery, and so on.

The subsystems of orthopedic surgical system 100 (i.e., virtual planning system 102, planning support system 104, manufacturing and delivery system 106, intraoperative guidance system 108, medical education system 110, pre- and postoperative monitoring system 112, and predictive analytics system 114) may include various systems. The systems in the subsystems of orthopedic surgical system 100 may include various types of computing systems, computing devices, including server computers, personal computers, tablet computers, smartphones, display devices, Internet of Things (IoT) devices, visualization devices (e.g., mixed reality (MR) visualization devices, virtual reality (VR) visualization devices, holographic projectors, or other devices for presenting extended reality (XR) visualizations), surgical tools, and so on. A holographic projector, in some examples, may project a hologram for general viewing by multiple users or a single user without a headset, rather than viewing only by a user wearing a headset. For example, virtual planning system 102 may include a MR visualization device and one or more server devices, planning support system 104 may include one or more personal computers and one or more server devices, and so on. A computing system is a set of one or more computing systems configured to operate as a system. In some examples, one or more devices may be shared between two or more of the subsystems of orthopedic surgical system 100. For instance, in the previous examples, virtual planning system 102 and planning support system 104 may include the same server devices.

In the example of FIG. 1, the devices included in the subsystems of orthopedic surgical system 100 may communicate using communications network 116. Communications network 116 may include various types of communication networks including one or more wide-area networks, such as the Internet, local area networks, and so on. In some examples, communications network 116 may include wired and/or wireless communication links.

Figure 2:
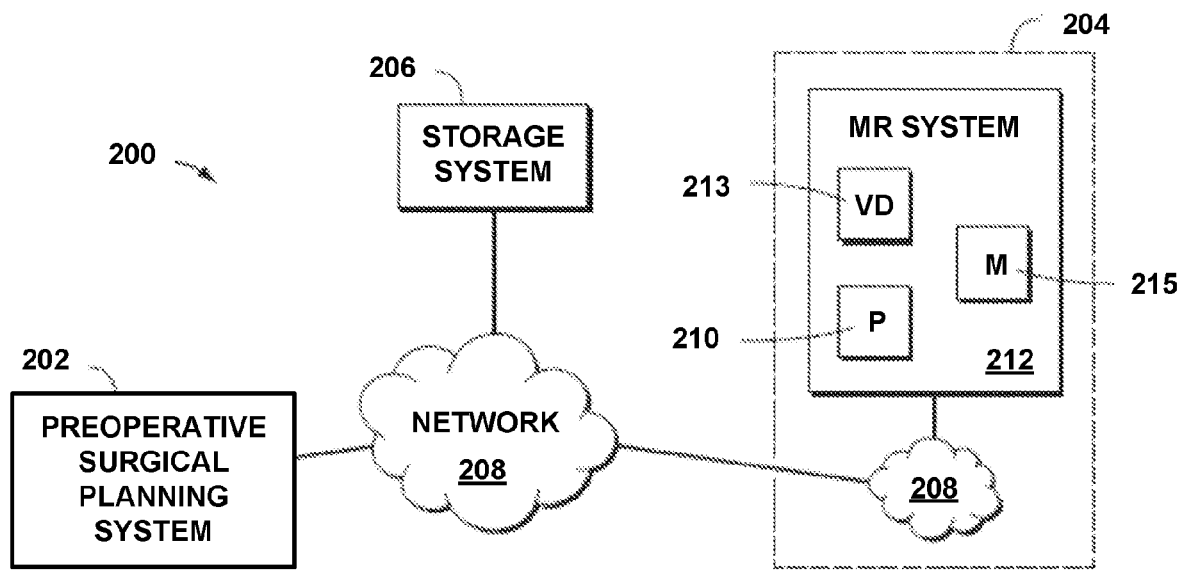
FIG. 2 is a block diagram of an orthopedic surgical system that includes a mixed reality (MR) system, according to an example of this disclosure.

Many variations of orthopedic surgical system 100 are possible in accordance with techniques of this disclosure. Such variations may include more or fewer subsystems than the version of orthopedic surgical system 100 shown in FIG. 1. For example, FIG. 2 is a block diagram of an orthopedic surgical system 200 that includes one or more mixed reality (MR) systems, according to an example of this disclosure. Orthopedic surgical system 200 may be used for creating, verifying, updating, modifying and/or implementing a surgical plan. In some examples, the surgical plan can be created preoperatively, such as by using a virtual surgical planning system (e.g., the BLUEPRINT™ system), and then verified, modified, updated, and viewed intraoperatively, e.g., using MR visualization of the surgical plan. In other examples, orthopedic surgical system 200 can be used to create the surgical plan immediately prior to surgery or intraoperatively, as needed. In some examples, orthopedic surgical system 200 may be used for surgical tracking, in which case orthopedic surgical system 200 may be referred to as a surgical tracking system. In other cases, orthopedic surgical system 200 may be generally referred to as a medical device system.

In the example of FIG. 2, orthopedic surgical system 200 includes a preoperative surgical planning system 202, a healthcare facility 204 (e.g., a surgical center or hospital), a storage system 206, and a network 208 that allows a user at healthcare facility 204 to access stored patient information, such as medical history, image data corresponding to the damaged joint or bone and various parameters corresponding to a surgical plan that has been created preoperatively (as examples). Preoperative surgical planning system 202 may be equivalent to virtual planning system 102 of FIG. 1 and, in some examples, may generally correspond to a virtual planning system similar or identical to the BLUEPRINT™ system.

In the example of FIG. 2, healthcare facility 204 includes a mixed reality (MR) system 212. In some examples of this disclosure, MR system 212 includes one or more processing device(s) (P) 210 to provide functionalities that will be described in further detail below. Processing device(s) 210 may also be referred to as processor(s). In addition, one or more users of MR system 212 (e.g., a surgeon, nurse, or other care provider) can use processing device(s) (P) 210 to generate a request for a particular surgical plan or other patient information that is transmitted to storage system 206 via network 208. In response, storage system 206 returns the requested patient information to MR system 212. In some examples, the users can use other processing device(s) to request and receive information, such as one or more processing devices that are part of MR system 212, but not part of any visualization device, or one or more processing devices that are part of a visualization device (e.g., visualization device 213) of MR system 212, or a combination of one or more processing devices that are part of MR system 212, but not part of any visualization device, and one or more processing devices that are part of a visualization device (e.g., visualization device 213) that is part of MR system 212.

In some examples, multiple users can simultaneously use MR system 212. For example, MR system 212 can be used in a spectator mode in which multiple users each use their own visualization devices so that the users can view the same information at the same time and from the same point of view. In some examples, MR system 212 may be used in a mode in which multiple users each use their own visualization devices so that the users can view the same information from different points of view. Different users may be located locally or remotely relative to one another, while interacting within MR system 212. If one or more users are remote, then those remote users may view similar virtual information to that of other local users while viewing different real-world views than the local users.

In some examples, processing device(s) 210 can provide a user interface to display data and receive input from users at healthcare facility 204. Processing device(s) 210 may be configured to control visualization device 213 to present a user interface. Furthermore, processing device(s) 210 may be configured to control visualization device 213 to present virtual images, such as 3D virtual models, 2D images, and so on. Processing device(s) 210 can include a variety of different processing or computing devices, such as servers, desktop computers, laptop computers, tablets, mobile phones and other electronic computing devices, or processors within such devices. In some examples, one or more of processing device(s) 210 can be located remote from healthcare facility 204. In some examples, processing device(s) 210 reside within visualization device 213. In some examples, at least one of processing device(s) 210 is external to visualization device 213. In some examples, one or more processing device(s) 210 reside within visualization device 213 and one or more of processing device(s) 210 are external to visualization device 213.

In the example of FIG. 2, MR system 212 also includes one or more memory or storage device(s) (M) 215 for storing data and instructions of software that can be executed by processing device(s) 210. The instructions of software can correspond to the functionality of MR system 212 described herein. In some examples, the functionalities of a virtual surgical planning application, such as the BLUEPRINT™ system, can also be stored and executed by processing device(s) 210 in conjunction with memory storage device(s) (M) 215. For instance, memory or storage system 215 may be configured to store data corresponding to at least a portion of a virtual surgical plan. In some examples, storage system 206 may be configured to store data corresponding to at least a portion of a virtual surgical plan. In some examples, memory or storage device(s) (M) 215 reside within visualization device 213. In some examples, memory or storage device(s) (M) 215 are external to visualization device 213. In some examples, memory or storage device(s) (M) 215 include a combination of one or more memory or storage devices within visualization device 213 and one or more memory or storage devices external to the visualization device.

Network 208 may be equivalent to network 116. Network 208 can include one or more wide area networks, local area networks, and/or global networks (e.g., the Internet) that connect preoperative surgical planning system 202 and MR system 212 to storage system 206. Storage system 206 can include one or more databases that can contain patient information, medical information, patient image data, and parameters that define the surgical plans. For example, medical images of the patient's diseased or damaged bone typically are generated preoperatively in preparation for an orthopedic surgical procedure. The medical images can include images of the relevant bone(s) taken along the sagittal plane and the coronal plane of the patient's body. The medical images can include X-ray images, magnetic resonance imaging (MRI) images, computerized tomography (CT) images, ultrasound images, and/or any other type of 2D or 3D image that provides information about the relevant surgical area. Storage system 206 also can include data identifying the implant components selected for a particular patient (e.g., type, size, etc.), surgical guides selected for a particular patient, and details of the surgical procedure, such as entry points, cutting planes, drilling axes, reaming depths, etc. Storage system 206 can be a cloud-based storage system (as shown) or can be located at healthcare facility 204 or at the location of preoperative surgical planning system 202 or can be part of MR system 212 or visualization device (VD) 213, as examples.

MR system 212 can be used by a surgeon before (e.g., preoperatively) or during the surgical procedure (e.g., intraoperatively) to create, review, verify, update, modify and/or implement a surgical plan. In some examples, MR system 212 may also be used after the surgical procedure (e.g., postoperatively) to review the results of the surgical procedure, assess whether revisions are required, or perform other postoperative tasks. To that end, MR system 212 may include a visualization device 213 that may be worn by the surgeon and (as will be explained in further detail below) is operable to display a variety of types of information, including a 3D virtual image of the patient's diseased, damaged, or postsurgical joint and details of the surgical plan, such as a 3D virtual image of the prosthetic implant components selected for the surgical plan, 3D virtual images of entry points for positioning the prosthetic components, alignment axes and cutting planes for aligning cutting or reaming tools to shape the bone surfaces, or drilling tools to define one or more holes in the bone surfaces, in the surgical procedure to properly orient and position the prosthetic components, surgical guides and instruments and their placement on the damaged joint, and any other information that may be useful to the surgeon to implement the surgical plan. MR system 212 can generate images of this information that are perceptible to the user of the visualization device 213 before and/or during the surgical procedure.

In some examples, MR system 212 includes multiple visualization devices (e.g., multiple instances of visualization device 213) so that multiple users can simultaneously see the same images and share the same 3D scene. In some such examples, one of the visualization devices can be designated as the master device and the other visualization devices can be designated as observers or spectators. Any observer device can be re-designated as the master device at any time, as may be desired by the users of MR system 212.

In this way, FIG. 2 illustrates a surgical planning system that includes a preoperative surgical planning system 202 to generate a virtual surgical plan customized to repair an anatomy of interest of a particular patient. For example, the virtual surgical plan may include a plan for an orthopedic joint repair surgical procedure, such as one of a standard total shoulder arthroplasty or a reverse shoulder arthroplasty. In this example, details of the virtual surgical plan may include details relating to at least one of preparation of glenoid bone or preparation of humeral bone. In some examples, the orthopedic joint repair surgical procedure is one of a stemless standard total shoulder arthroplasty, a stemmed standard total shoulder arthroplasty, a stemless reverse shoulder arthroplasty, a stemmed reverse shoulder arthroplasty, an augmented glenoid standard total shoulder arthroplasty, and an augmented glenoid reverse shoulder arthroplasty.

The virtual surgical plan may include a 3D virtual model corresponding to the anatomy of interest of the particular patient and a 3D model of a prosthetic component matched to the particular patient to repair the anatomy of interest or selected to repair the anatomy of interest. Furthermore, in the example of FIG. 2, the surgical planning system includes a storage system 206 to store data corresponding to the virtual surgical plan. The surgical planning system of FIG. 2 also includes MR system 212, which may comprise visualization device 213. In some examples, visualization device 213 is wearable by a user. In some examples, visualization device 213 is held by a user, or rests on a surface in a place accessible to the user. MR system 212 may be configured to present a user interface via visualization device 213. The user interface is visually perceptible to the user using visualization device 213. For instance, in one example, a screen of visualization device 213 may display real-world images and the user interface on a screen. In some examples, visualization device 213 may project virtual, holographic images onto see-through holographic lenses and also permit a user to see real-world objects of a real-world environment through the lenses. In other words, visualization device 213 may comprise one or more see-through holographic lenses and one or more display devices that present imagery to the user via the holographic lenses to present the user interface to the user.

In some examples, visualization device 213 is configured such that the user can manipulate the user interface (which is visually perceptible to the user when the user is wearing or otherwise using visualization device 213) to request and view details of the virtual surgical plan for the particular patient, including a 3D virtual model of the anatomy of interest (e.g., a 3D virtual bone of the anatomy of interest) and a 3D model of the prosthetic component selected to repair an anatomy of interest. In some such examples, visualization device 213 is configured such that the user can manipulate the user interface so that the user can view the virtual surgical plan intraoperatively, including (at least in some examples) the 3D virtual model of the anatomy of interest (e.g., a 3D virtual bone of the anatomy of interest). In some examples, MR system 212 can be operated in an augmented surgery mode in which the user can manipulate the user interface intraoperatively so that the user can visually perceive details of the virtual surgical plan projected in a real environment, e.g., on a real anatomy of interest of the particular patient. In this disclosure, the terms real and real world may be used in a similar manner. For example, MR system 212 may present one or more virtual objects that provide guidance for preparation of a bone surface and placement of a prosthetic implant on the bone surface. Visualization device 213 may present one or more virtual objects in a manner in which the virtual objects appear to be overlaid on an actual, real anatomical object of the patient, within a real-world environment, e.g., by displaying the virtual object(s) with actual, real-world patient anatomy viewed by the user through holographic lenses. For example, the virtual objects may be 3D virtual objects that appear to reside within the real-world environment with the actual, real anatomical object.

Figure 3:
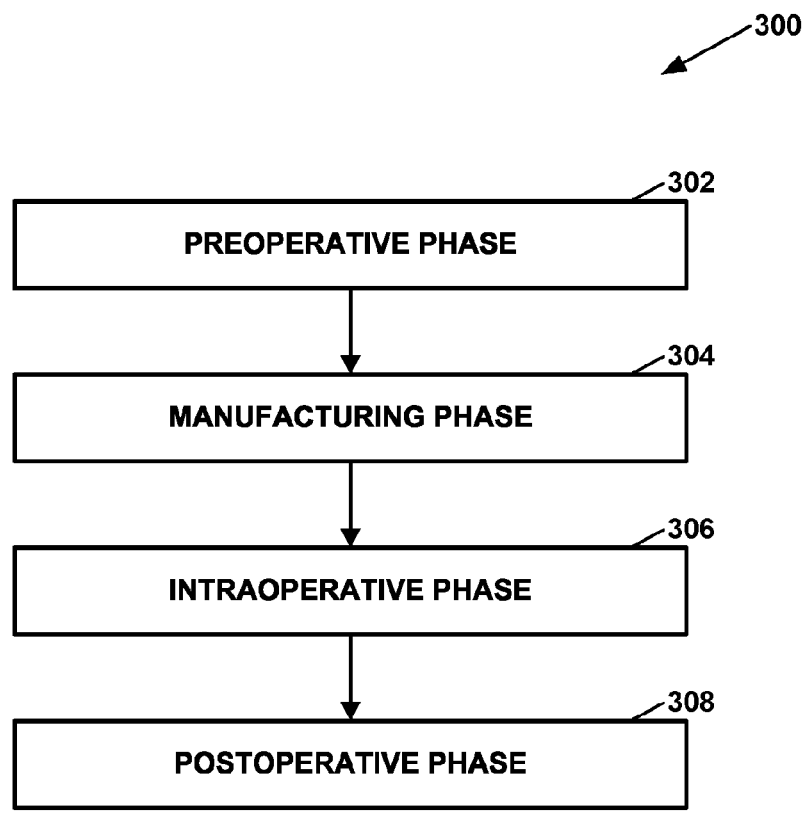
FIG. 3 is a flowchart illustrating example phases of a surgical lifecycle.

FIG. 3 is a flowchart illustrating example phases of a surgical lifecycle 300. In the example of FIG. 3, surgical lifecycle 300 begins with a preoperative phase (302). During the preoperative phase, a surgical plan is developed. The preoperative phase may be followed by a manufacturing and delivery phase (304). During the manufacturing and delivery phase, patient-specific items, such as parts and equipment, needed for executing the surgical plan are manufactured and delivered to a surgical site. For instance, a patient specific implant may be manufactured based on a design generated during the preoperative phase. An intraoperative phase follows the manufacturing and delivery phase (306). The surgical plan is executed during the intraoperative phase. In other words, one or more persons perform the surgery on the patient during the intraoperative phase. The intraoperative phase is followed by the postoperative phase (308). The postoperative phase includes activities occurring after the surgical plan is complete. For example, the patient may be monitored during the postoperative phase for complications.

As described in this disclosure, orthopedic surgical system 100 (FIG. 1) may be used in one or more of preoperative phase 302, the manufacturing and delivery phase 304, the intraoperative phase 306, and the postoperative phase 308. For example, virtual planning system 102 and planning support system 104 may be used in preoperative phase 302. Manufacturing and delivery system 106 may be used in the manufacturing and delivery phase 304. Intraoperative guidance system 108 may be used in intraoperative phase 306. Some of the systems of FIG. 1 may be used in multiple phases of FIG. 3. For example, medical education system 110 may be used in one or more of preoperative phase 302, intraoperative phase 306, and postoperative phase 308; pre- and postoperative monitoring system 112 may be used in preoperative phase 302 and postoperative phase 308. Predictive analytics system 114 may be used in preoperative phase 302 and postoperative phase 308.

Figure 4:
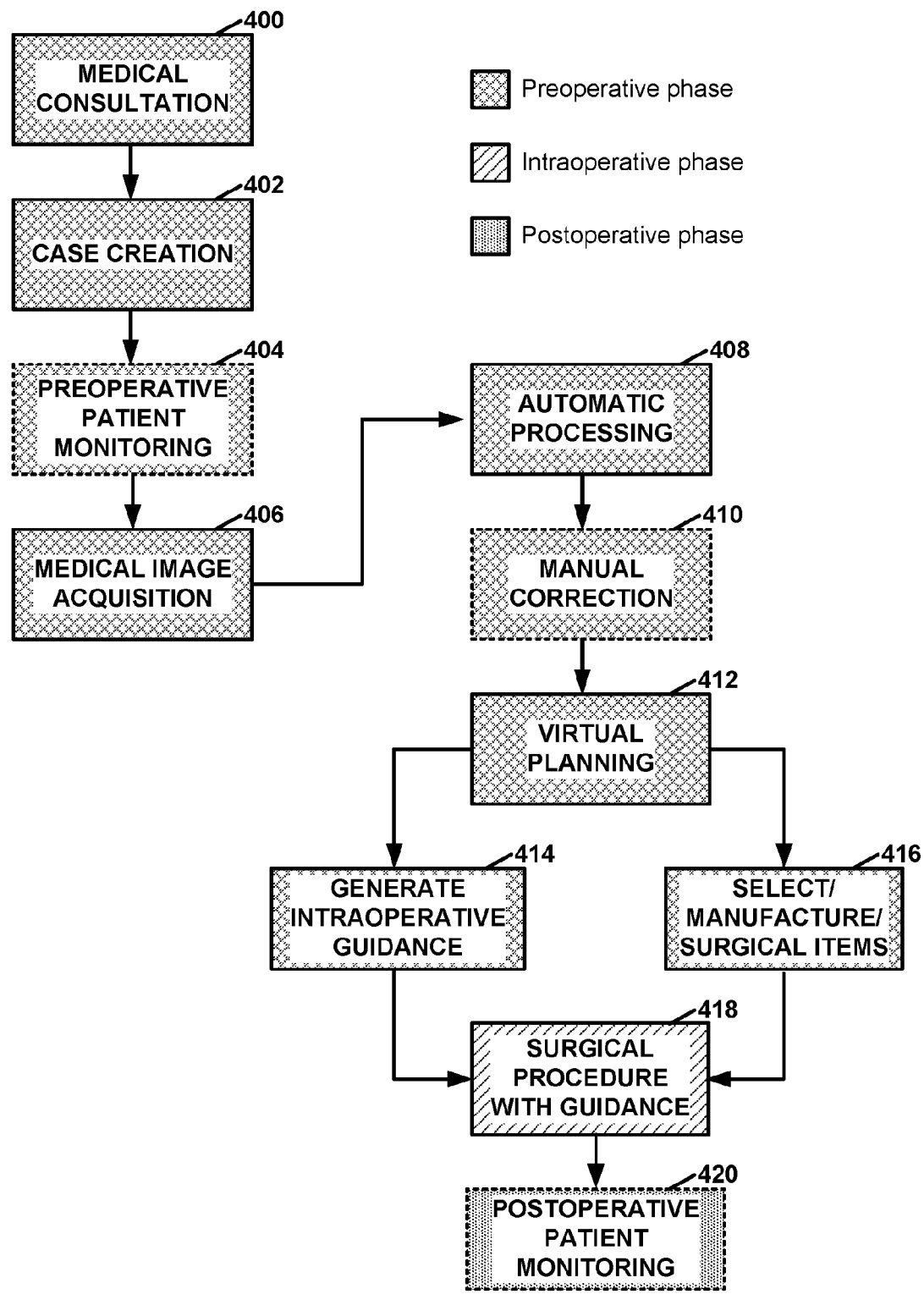
FIG. 4 is a flowchart illustrating preoperative, intraoperative and postoperative workflows in support of an orthopedic surgical procedure.

Various workflows may exist within the surgical process of FIG. 3. For example, different workflows within the surgical process of FIG. 3 may be appropriate for different types of surgeries. FIG. 4 is a flowchart illustrating preoperative, intraoperative and postoperative workflows in support of an orthopedic surgical procedure. In the example of FIG. 4, the surgical process begins with a medical consultation (400). During the medical consultation (400), a healthcare professional evaluates a medical condition of a patient. For instance, the healthcare professional may consult the patient with respect to the patient's symptoms. During the medical consultation (400), the healthcare professional may also discuss various treatment options with the patient. For instance, the healthcare professional may describe one or more different surgeries to address the patient's symptoms.

Furthermore, the example of FIG. 4 includes a case creation step (402). In other examples, the case creation step occurs before the medical consultation step. During the case creation step, the medical professional or other user establishes an electronic case file for the patient. The electronic case file for the patient may include information related to the patient, such as data regarding the patient's symptoms, patient range of motion observations, data regarding a surgical plan for the patient, medical images of the patients, notes regarding the patient, billing information regarding the patient, and so on.

The example of FIG. 4 includes a preoperative patient monitoring phase (404). During the preoperative patient monitoring phase, the patient's symptoms may be monitored. For example, the patient may be suffering from pain associated with arthritis in the patient's shoulder. In this example, the patient's symptoms may not yet rise to the level of requiring an arthroplasty to replace the patient's shoulder. However, arthritis typically worsens over time. Accordingly, the patient's symptoms may be monitored to determine whether the time has come to perform a surgery on the patient's shoulder. Observations from the preoperative patient monitoring phase may be stored in the electronic case file for the patient. In some examples, predictive analytics system 114 may be used to predict when the patient may need surgery, to predict a course of treatment to delay or avoid surgery or make other predictions with respect to the patient's health.

Additionally, in the example of FIG. 4, a medical image acquisition step occurs during the preoperative phase (406). During the image acquisition step, medical images of the patient are generated. The medical images may be generated in a variety of ways. For instance, the images may be generated using a Computed Tomography (CT) process, a Magnetic Resonance Imaging (MRI) process, an ultrasound process, or another imaging process. The medical images generated during the image acquisition step include images of an anatomy of interest of the patient. For instance, if the patient's symptoms involve the patient's shoulder, medical images of the patient's shoulder may be generated. The medical images may be added to the patient's electronic case file. Healthcare professionals may be able to use the medical images in one or more of the preoperative, intraoperative, and postoperative phases. In some examples, the medical images may be segmented into anatomical parts. For instance, medical images of the patient's shoulder may be segmented into a scapula, a humerus, etc. Three-dimensional (3D) models of the anatomical parts may be generated.

Furthermore, in the example of FIG. 4, an automatic processing step may occur (408). During the automatic processing step, virtual planning system 102 (FIG. 1) may automatically develop a preliminary surgical plan for the patient. In some examples of this disclosure, virtual planning system 102 may use machine learning techniques to develop the preliminary surgical plan based on information in the patient's virtual case file.

The example of FIG. 4 also includes a manual correction step (410). During the manual correction step, one or more human users may check and correct the determinations made during the automatic processing step. In some examples of this disclosure, one or more users may use mixed reality or virtual reality visualization devices during the manual correction step. In some examples, changes made during the manual correction step may be used as training data to refine the machine learning techniques applied by virtual planning system 102 during the automatic processing step.

A virtual planning step (412) may follow the manual correction step in FIG. 4. During the virtual planning step, a healthcare professional may develop a surgical plan for the patient. In some examples of this disclosure, one or more users may use mixed reality or virtual reality visualization devices during development of the surgical plan for the patient. As discussed in further detail below, during the virtual planning step, virtual planning system 102 may design a patient matched implant.

Furthermore, in the example of FIG. 4, intraoperative guidance may be generated (414). The intraoperative guidance may include guidance to a surgeon on how to execute the surgical plan. In some examples of this disclosure, virtual planning system 102 may generate at least part of the intraoperative guidance. In some examples, the surgeon or other user may contribute to the intraoperative guidance.

Additionally, in the example of FIG. 4, a step of selecting and manufacturing surgical items is performed (416). During the step of selecting and manufacturing surgical items, manufacturing and delivery system 106 (FIG. 1) may manufacture surgical items for use during the surgery described by the surgical plan. For example, the surgical items may include surgical implants (e.g., generic and/or patient specific), surgical tools, and other items required to perform the surgery described by the surgical plan.

In the example of FIG. 4, a surgical procedure may be performed with guidance from intraoperative system 108 (FIG. 1) (418). For example, a surgeon may perform the surgery while wearing a head-mounted MR visualization device of intraoperative system 108 that presents guidance information to the surgeon. The guidance information may help guide the surgeon through the surgery, providing guidance for various surgical steps in a surgical workflow, including sequence of surgical steps, details of individual surgical steps, and tool or implant selection, implant placement and position, and bone surface preparation for various surgical steps in the surgical procedure workflow.

Postoperative patient monitoring may occur after completion of the surgical procedure (420). During the postoperative patient monitoring step, healthcare outcomes of the patient may be monitored. Healthcare outcomes may include relief from symptoms, ranges of motion, complications, performance of implanted surgical items, and so on. Pre- and postoperative monitoring system 112 (FIG. 1) may assist in the postoperative patient monitoring step.

The medical consultation, case creation, preoperative patient monitoring, image acquisition, automatic processing, manual correction, and virtual planning steps of FIG. 4 are part of preoperative phase 302 of FIG. 3. The surgical procedures with guidance steps of FIG. 4 is part of intraoperative phase 306 of FIG. 3. The postoperative patient monitoring step of FIG. 4 is part of postoperative phase 308 of FIG. 3.

As mentioned above, one or more of the subsystems of orthopedic surgical system 100 may include one or more mixed reality (MR) systems, such as MR system 212 (FIG. 2). Each MR system may include a visualization device. For instance, in the example of FIG. 2, MR system 212 includes visualization device 213. In some examples, in addition to including a visualization device, an MR system may include external computing resources that support the operations of the visualization device. For instance, the visualization device of an MR system may be communicatively coupled to a computing device (e.g., a personal computer, backpack computer, smartphone, etc.) that provides the external computing resources. Alternatively, adequate computing resources may be provided on or within visualization device 213 to perform necessary functions of the visualization device.

Figure 5:
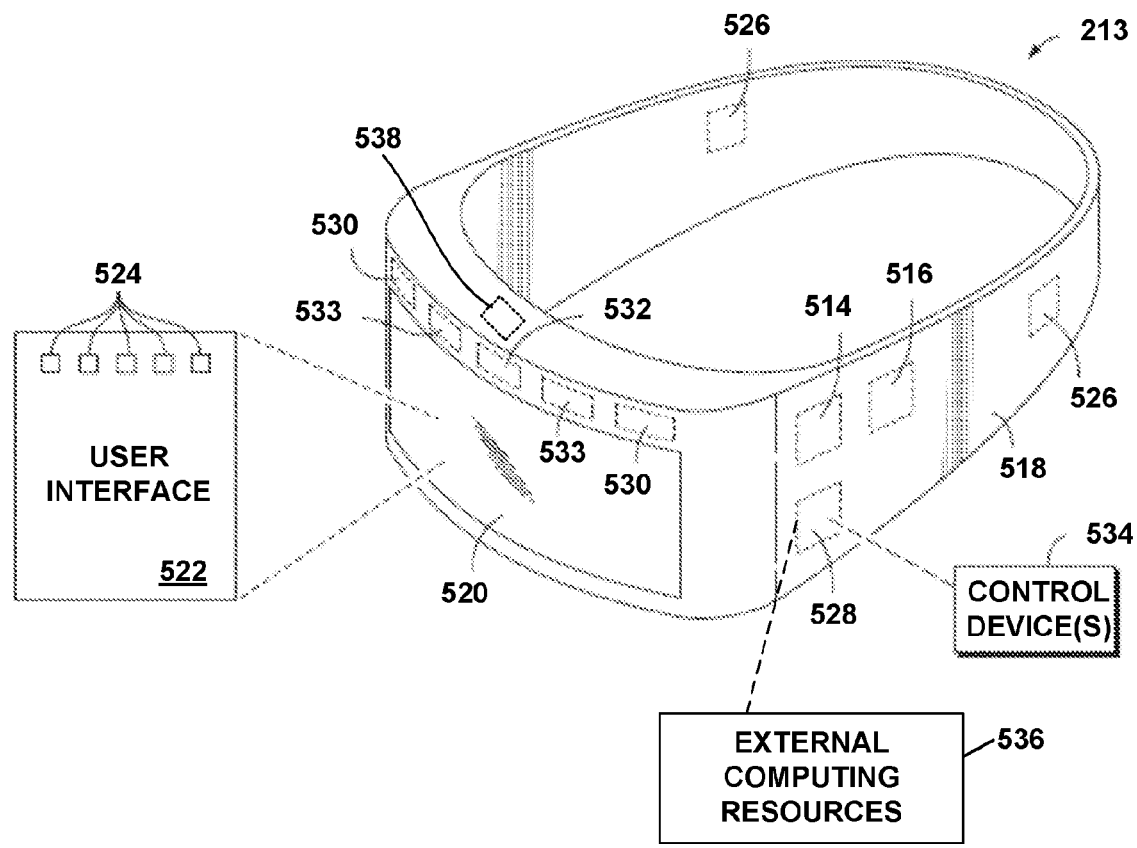
FIG. 5 is a schematic representation of a visualization device for use in a mixed reality (MR) system, according to an example of this disclosure.

FIG. 5 is a schematic representation of visualization device 213 for use in an MR system, such as MR system 212 of FIG. 2, according to an example of this disclosure. As shown in the example of FIG. 5, visualization device 213 can include a variety of electronic components found in a computing system, including one or more processor(s) 514 (e.g., microprocessors or other types of processing units) and memory 516 that may be mounted on or within a frame 518. Furthermore, in the example of FIG. 5, visualization device 213 may include a transparent screen 520 that is positioned at eye level when visualization device 213 is worn by a user. In some examples, screen 520 can include one or more liquid crystal displays (LCDs) or other types of display screens on which images are perceptible to a surgeon who is wearing or otherwise using visualization device 213 via screen 520. Other display examples include organic light emitting diode (OLED) displays. In some examples, visualization device 213 can operate to project 3D images onto the user's retinas using techniques known in the art.

In some examples, screen 520 includes see-through holographic lenses, sometimes referred to as waveguides, that permit a user to see real-world objects through (e.g., beyond) the lenses and also see holographic imagery projected into the lenses and onto the user's retinas by displays, such as liquid crystal on silicon (LCoS) display devices, which are sometimes referred to as light engines or projectors, operating as an example of a holographic projection system 538 within visualization device 213. In other words, visualization device 213 may include one or more see-through holographic lenses to present virtual images to a user. Hence, in some examples, visualization device 213 can operate to project 3D images onto the user's retinas via screen 520, e.g., formed by holographic lenses. In this manner, visualization device 213 may be configured to present a 3D virtual image to a user within a real-world view observed through screen 520, e.g., such that the virtual image appears to form part of the real-world environment. In some examples, visualization device 213 may be a Microsoft HOLOLENS™ headset, available from Microsoft Corporation, of Redmond, Washington, USA, or a similar device, such as, for example, a similar MR visualization device that includes waveguides. The HOLOLENS™ device can be used to present 3D virtual objects via holographic lenses, or waveguides, while permitting a user to view actual objects in a real-world scene, i.e., in a real-world environment, through the holographic lenses.

Although the example of FIG. 5 illustrates visualization device 213 as a head-wearable device, visualization device 213 may have other forms and form factors. For instance, in some examples, visualization device 213 may be a handheld smartphone or tablet.

Visualization device 213 can also generate a virtual user interface (UI) 522 that is visible to the user, e.g., as holographic imagery projected into see-through holographic lenses as described above. For example, UI 522 can include a variety of selectable virtual widgets 524 that allow the user to interact with a mixed reality (MR) system, such as MR system 212 of FIG. 2. Imagery presented by visualization device 213 may include, for example, one or more 3D virtual objects. Details of an example of UI 522 are described elsewhere in this disclosure. Visualization device 213 also can include a speaker or other sensory devices 526 that may be positioned adjacent the user's ears. Sensory devices 526 can convey audible information or other perceptible information (e.g., vibrations) to assist the user of visualization device 213.

Visualization device 213 can also include a transceiver 528 to connect visualization device 213 to a processing device 510 and/or to network 208 and/or to a computing cloud, such as via a wired communication protocol or a wireless protocol, e.g., Wi-Fi, Bluetooth, etc. Visualization device 213 also includes a variety of sensors to collect sensor data, such as one or more optical camera(s) 530 (or other optical sensors) and one or more depth camera(s) 532 (or other depth sensors), mounted to, on or within frame 518. In some examples, the optical sensor(s) 530 are operable to scan the geometry of the physical environment in which a user of MR system 212 is located (e.g., an operating room) and collect two-dimensional (2D) optical image data (either monochrome or color). Depth sensor(s) 532 are operable to provide 3D image data, such as by employing time of flight, stereo or other known or future-developed techniques for determining depth and thereby generating image data in three dimensions. Other sensors can include motion sensors 533 (e.g., Inertial Mass Unit (IMU) sensors, accelerometers, etc.) to assist with tracking movement.

MR system 212 processes the sensor data so that geometric, environmental, textural, or other types of landmarks (e.g., corners, edges or other lines, walls, floors, objects) in the user's environment or "scene" can be defined and movements within the scene can be detected. As an example, the various types of sensor data can be combined or fused so that the user of visualization device 213 can perceive 3D images that can be positioned, or fixed and/or moved within the scene. When a 3D image is fixed in the scene, the user can walk around the 3D image, view the 3D image from different perspectives, and manipulate the 3D image within the scene using hand gestures, voice commands, gaze line (or direction) and/or other control inputs. As another example, the sensor data can be processed so that the user can position a 3D virtual object (e.g., a bone model) on an observed physical object in the scene (e.g., a surface, the patient's real bone, etc.) and/or orient the 3D virtual object with other virtual images displayed in the scene. In some examples, the sensor data can be processed so that the user can position and fix a virtual representation of the surgical plan (or other widget, image or information) onto a surface, such as a wall of the operating room. Yet further, in some examples, the sensor data can be used to recognize surgical instruments and the position and/or location of those instruments.

Visualization device 213 may include one or more processors 514 and memory 516, e.g., within frame 518 of the visualization device. In some examples, one or more external computing resources 536 process and store information, such as sensor data, instead of or in addition to in-frame processor(s) 514 and memory 516. In this way, data processing and storage may be performed by one or more processors 514 and memory 516 within visualization device 213 and/or some of the processing and storage requirements may be offloaded from visualization device 213. Hence, in some examples, one or more processors that control the operation of visualization device 213 may be within visualization device 213, e.g., as processor(s) 514. Alternatively, in some examples, at least one of the processors that controls the operation of visualization device 213 may be external to visualization device 213, e.g., as processor(s) 210. Likewise, operation of visualization device 213 may, in some examples, be controlled in part by a combination one or more processors 514 within the visualization device and one or more processors 210 external to visualization device 213.

For instance, in some examples, when visualization device 213 is in the context of FIG. 2, processing of the sensor data can be performed by processing device(s) 210 in conjunction with memory or storage device(s) (M) 215. In some examples, processor(s) 514 and memory 516 mounted to frame 518 may provide sufficient computing resources to process the sensor data collected by cameras 530, 532 and motion sensors 533. In some examples, the sensor data can be processed using a Simultaneous Localization and Mapping (SLAM) algorithm, or other known or future-developed algorithms for processing and mapping 2D and 3D image data and tracking the position of visualization device 213 in the 3D scene. In some examples, image tracking may be performed using sensor processing and tracking functionality provided by the Microsoft HOLOLENS™ system, e.g., by one or more sensors and processors 514 within a visualization device 213 substantially conforming to the Microsoft HOLOLENS™ device or a similar mixed reality (MR) visualization device.

In some examples, MR system 212 can also include user-operated control device(s) 534 that allow the user to operate MR system 212, use MR system 212 in spectator mode (either as master or observer), interact with UI 522 and/or otherwise provide commands or requests to processing device(s) 210 or other systems connected to network 208. As examples, control device(s) 534 can include a microphone, a touch pad, a control panel, a motion sensor or other types of control input devices with which the user can interact.

Figure 6:
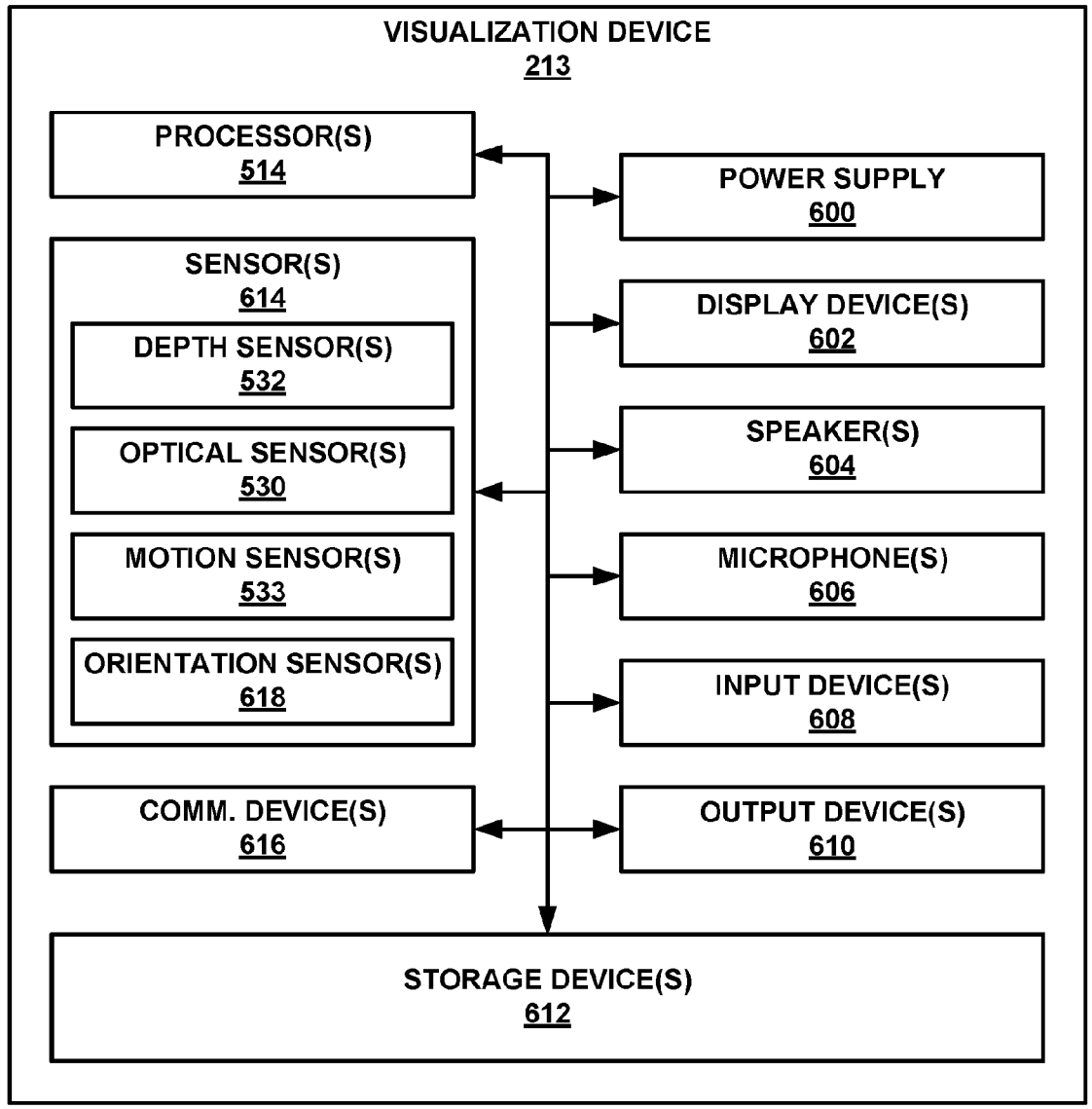
FIG. 6 is a block diagram illustrating example components of a visualization device for use in a mixed reality (MR) system, according to an example of this disclosure.

FIG. 6 is a block diagram illustrating example components of visualization device 213 for use in a MR system. In the example of FIG. 6, visualization device 213 includes processors 514, a power supply 600, display device(s) 602, speakers 604, microphone(s) 606, input device(s) 608, output device(s) 610, storage device(s) 612, sensor(s) 614, and communication devices 616. In the example of FIG. 6, sensor(s) 616 may include depth sensor(s) 532, optical sensor(s) 530, motion sensor(s) 533, and orientation sensor(s) 618. Optical sensor(s) 530 may include cameras, such as Red-Green-Blue (RGB) video cameras, infrared cameras, or other types of sensors that form images from light. Display device(s) 602 may display imagery to present a user interface to the user.

Speakers 604, in some examples, may form part of sensory devices 526 shown in FIG. 5. In some examples, display devices 602 may include screen 520 shown in FIG. 5. For example, as discussed with reference to FIG. 5, display device(s) 602 may include see-through holographic lenses, in combination with projectors, that permit a user to see real-world objects, in a real-world environment, through the lenses, and also see virtual 3D holographic imagery projected into the lenses and onto the user's retinas, e.g., by a holographic projection system. In this example, virtual 3D holographic objects may appear to be placed within the real-world environment. In some examples, display devices 602 include one or more display screens, such as LCD display screens, OLED display screens, and so on. The user interface may present virtual images of details of the virtual surgical plan for a particular patient.

In some examples, a user may interact with and control visualization device 213 in a variety of ways. For example, microphones 606, and associated speech recognition processing circuitry or software, may recognize voice commands spoken by the user and, in response, perform any of a variety of operations, such as selection, activation, or deactivation of various functions associated with surgical planning, intra-operative guidance, or the like. As another example, one or more cameras or other optical sensors 530 of sensors 614 may detect and interpret gestures (such as hand motions, hand gestures, finger motions, finger gestures, eye blinks, or other physical gestures) in order to perform operations as described above. As a further example, sensors 614 may sense gaze direction and perform various operations as described elsewhere in this disclosure. In some examples, input devices 608 may receive manual input from a user, e.g., via a handheld controller including one or more buttons, a keypad, a touchscreen, joystick, trackball, and/or other manual input media, and perform, in response to the manual user input, various operations as described above.

As discussed above, surgical lifecycle 300 may include a preoperative phase 302 (FIG. 3). One or more users may use orthopedic surgical system 100 in preoperative phase 302. For instance, orthopedic surgical system 100 may include virtual planning system 102 to help the one or more users generate a virtual surgical plan that may be customized to an anatomy of interest of a particular patient. As described herein, the virtual surgical plan may include a 3-dimensional virtual model that corresponds to the anatomy of interest of the particular patient and a 3-dimensional model of one or more prosthetic components matched to the particular patient to repair the anatomy of interest or selected to repair the anatomy of interest. The virtual surgical plan also may include a 3-dimensional virtual model of guidance information to guide a surgeon in performing the surgical procedure, e.g., in preparing bone surfaces or tissue and placing implantable prosthetic hardware relative to such bone surfaces or tissue.

A visualization system, such as MR visualization system 212, may be configured to display virtual guidance including one or more virtual guides for performing work on a portion of a patient's anatomy. In some examples, a user such as a surgeon may view real-world objects in a real-world scene. The real-world scene may be in a real-world environment such as a surgical operating room. In this disclosure, the terms real and real-world may be used in a similar manner. The real-world objects viewed by the user in the real-world scene may include the patient's actual, real anatomy, such as an actual glenoid or humerus, exposed during surgery. The user may view the real-world objects via a see-through (e.g., transparent) screen, such as see-through holographic lenses, of a head-mounted MR visualization device, such as visualization device 213, and also see virtual guidance such as virtual MR objects that appear to be projected on the screen or within the real-world scene, such that the MR guidance object(s) appear to be part of the real-world scene, e.g., with the virtual objects appearing to the user to be integrated with the actual, real-world scene. For example, the virtual guidance may be projected on the screen of a MR visualization device, such as visualization device 213, such that the virtual guidance is overlaid on, and appears to be placed within, an actual, observed view of the patient's actual bone viewed by the surgeon through the transparent screen, e.g., through see-through holographic lenses. Hence, in this example, the virtual guidance may be a virtual 3D object that appears to be part of the real-world environment, along with actual, real-world objects.

A screen through which the surgeon views the actual, real anatomy and also observes the virtual objects, such as virtual anatomy and/or virtual surgical guidance, may include one or more see-through holographic lenses. The holographic lenses, sometimes referred to as "waveguides," may permit the user to view real-world objects through the lenses and display projected holographic objects for viewing by the user. As discussed above, an example of a suitable head-mounted MR device for visualization device 213 is the Microsoft HOLOLENS™ headset, available from Microsoft Corporation, of Redmond, Washington, USA. The HOLO-LENS™ headset includes see-through, holographic lenses, also referred to as waveguides, in which projected images are presented to a user. The HOLOLENS™ headset also includes an internal computer, cameras and sensors, and a projection system to project the holographic content via the holographic lenses for viewing by the user. In general, the Microsoft HOLOLENS™ headset or a similar MR visualization device may include, as mentioned above, LCoS display devices that project images into holographic lenses, also referred to as waveguides, e.g., via optical components that couple light from the display devices to optical waveguides. The waveguides may permit a user to view a real-world scene through the waveguides while also viewing a 3D virtual image presented to the user via the waveguides. In some examples, the waveguides may be diffraction waveguides.

The visualization system (e.g., MR system 212/visualization device 213) may be configured to display different types of virtual guidance. Examples of virtual guidance include, but are not limited to, a virtual point, a virtual axis, a virtual angle, a virtual path, a virtual plane, virtual reticle, and a virtual surface or contour. As discussed above, the visualization system (e.g., MR system 212/visualization device 213) may enable a user to directly view the patient's anatomy via a lens by which the virtual guides are displayed, e.g., projected. The virtual guidance may guide or assist various aspects of the surgery. For instance, a virtual guide may guide at least one of preparation of anatomy for attachment of the prosthetic or attachment of the prosthetic to the anatomy.

The visualization system may obtain parameters for the virtual guides from a virtual surgical plan, such as the virtual surgical plan described herein. Example parameters for the virtual guides include, but are not necessarily limited to, guide location, guide orientation, guide type, guide color, etc.

The visualization system may display a virtual guide in a manner in which the virtual guide appears to be overlaid on an actual, real object, within a real-world environment, e.g., by displaying the virtual guide(s) with actual, real-world objects (e.g., at least a portion of the patient's anatomy) viewed by the user through holographic lenses. For example, the virtual guidance may be 3D virtual objects that appear to reside within the real-world environment with the actual, real object.

The techniques of this disclosure are described below with respect to a shoulder arthroplasty surgical procedure. Examples of shoulder arthroplasties include, but are not limited to, reversed arthroplasty, augmented reverse arthroplasty, standard total shoulder arthroplasty, augmented total shoulder arthroplasty, and hemiarthroplasty. However, the techniques are not so limited, and the visualization system may be used to provide virtual guidance information, including virtual guides in any type of surgical procedure. Other example procedures in which a visualization system, such as MR system 212, may be used to provide virtual guidance include, but are not limited to, other types of orthopedic surgeries; any type of procedure with the suffix "plasty," "stomy," "ectomy," "clasia," or "centesis,"; orthopedic surgeries for other joints, such as elbow, wrist, finger, hip, knee, ankle or toe, or any other orthopedic surgical procedure in which precision guidance is desirable. For instance, a visualization system may be used to provide virtual guidance for an ankle arthroplasty surgical procedure.

As discussed above, a MR system (e.g., MR system 212, MR system 1800A of FIG. 18, etc.) may receive a virtual surgical plan for attaching an implant to a patient and/or preparing bones, soft tissue or other anatomy of the patient to receive the implant. The virtual surgical plan may specify various surgical steps to be performed and various parameters for the surgical steps to be performed. As one example, the virtual surgical plan may specify a location on the patient's bone (e.g., glenoid, humerus, tibia, talus, etc.) for attachment of a guide pin. As another example, the virtual surgical plan may specify locations and/or orientations of one or more anchorage locations (e.g., screws, stems, pegs, keels, etc.).

Figure 7:
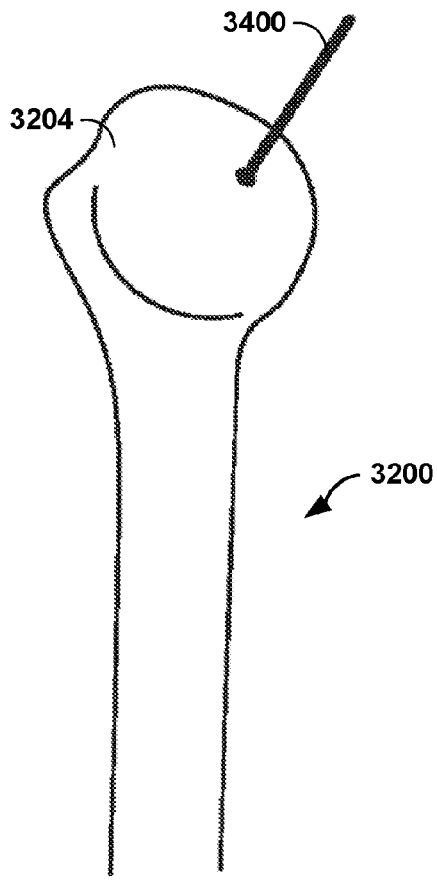
FIGS. 7 and 8 are conceptual diagrams illustrating an MR system providing virtual guidance for installation of a guide pin in a bone, in accordance with one or more techniques of this disclosure.
Figure 8:
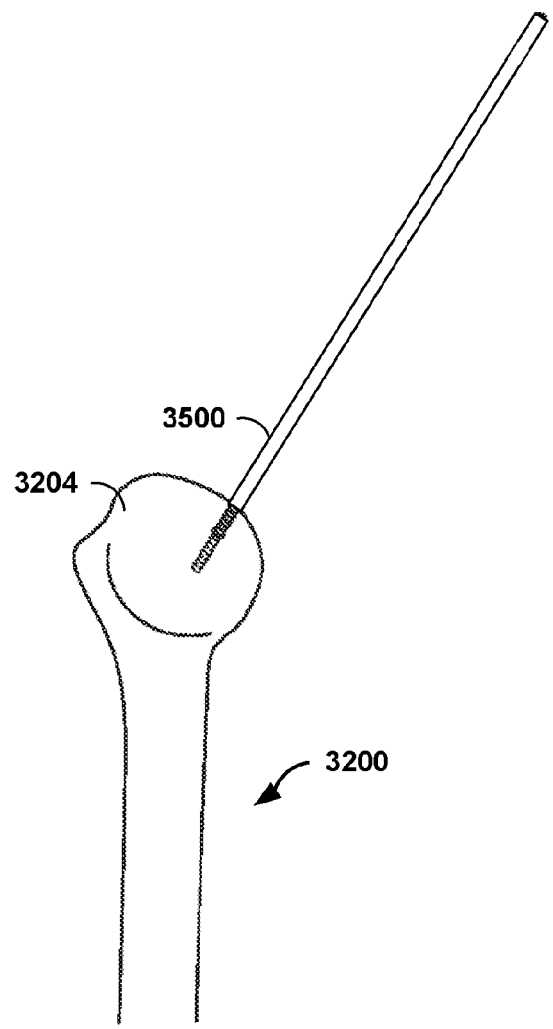

FIGS. 7 and 8 are conceptual diagrams illustrating an MR system providing virtual guidance for installation of a guide pin in a bone, in accordance with one or more techniques of this disclosure. In FIGS. 7 and 8 and other FIGS., for purposes of illustration, some of the surrounding tissue and some bone has been omitted for ease of illustration. As shown in FIG. 7, MR system 212 may display virtual axis 3400 on or relative to humeral head 3204 of humerus 3200. FIG. 7 and subsequent figures illustrate one example of what the surgeon, or other user, would see when viewing via visualization device 213. In particular, when viewing via visualization device 213 from the view shown in FIG. 7, the surgeon may see a portion of humerus 3200 and virtual axis 3400 (and/or other virtual guidance) overlaid on the portion of humerus 3200.

To display virtual axis 3400, MR system 212 may determine a location on a virtual model of humerus 3200 at which a guide is to be installed. MR system 212 may obtain the location from a virtual surgical plan (e.g., the virtual surgical plan described above as generated by virtual planning system 202). The location obtained by MR system 212 may specify one or both of coordinates of a point on the virtual model and a vector (e.g., a planned position and a planned orientation). The point may be the position at which the guide is to be installed and the vector may indicate the angle/slope at which the guide is to be installed. As such, MR system 212 may display a virtual drilling axis having parameters obtained from the virtual surgical plan, and the virtual drilling axis may be configured to guide drilling of one or more holes in the glenoid (e.g., for attachment of a guide pin to the scapula).

A virtual model of humerus 3200 may be registered with humerus 3200 such that coordinates on the virtual model approximately correspond to coordinates on humerus 3200. For instance, MR system 212 may generate a transformation matrix between the virtual model of humerus 3200 and an observed portion of humerus 3200. This transformation matrix may allow for translation along the x, y, and z axes of the virtual model and rotation about the x, y and z axes in order to achieve and maintain alignment between the virtual and observed bones. In some examples, after registration is complete, MR system 212 utilizes the results of the registration to perform simultaneous localization and mapping (SLAM) (or any other tracking algorithm) to maintain alignment of the virtual model to the corresponding observed object. As such, by displaying virtual axis 3400 at the determined location on the virtual model, MR system 212 may display virtual axis 3400 at the planned position on humerus 3200.

The surgeon may attach a guide pin (e.g., a surgical pin) to humerus 3200 using the displayed virtual guidance. For instance, where the guide pin includes a self-tapping threaded distal tip, the surgeon may align the guide pin with the displayed virtual axis 3400 and utilize a drill or other instrument to install the guide pin in humerus 3200.

FIG. 8 is a conceptual diagram illustrating guide 3500 as installed in humeral head 3204. Guide 3500 may take the form of an elongated pin to be mounted in a hole formed in the humeral head. As shown in FIGS. 7 and 8, by displaying virtual axis 3400, a surgeon may install guide 3500 at the planned position on humeral head 3204.

As discussed above, FIG. 7 illustrates an example of what the surgeon, or other user, would see when viewing via visualization device 213 from the view shown in FIG. 7. In particular, FIG. 7 shows what the surgeon would see when the surgeon's gaze line is from a side view/substantially orthogonal to the axis of the surgical step being performed (e.g., virtual axis 3400). However, the surgeon is not likely to view the patient from such an angle when operating a driver of a rotating tool (e.g., a drill or motor that rotates the guide pin (e.g., guide 3500), a drill bit, a reamer, or the like). Instead, when operating the driver of the rotating tool, the surgeon is likely to view the patient from behind the drill or motor while operating the drill or motor, with a gaze line substantially parallel to an axis of the surgical step being performed.

Figure 9:
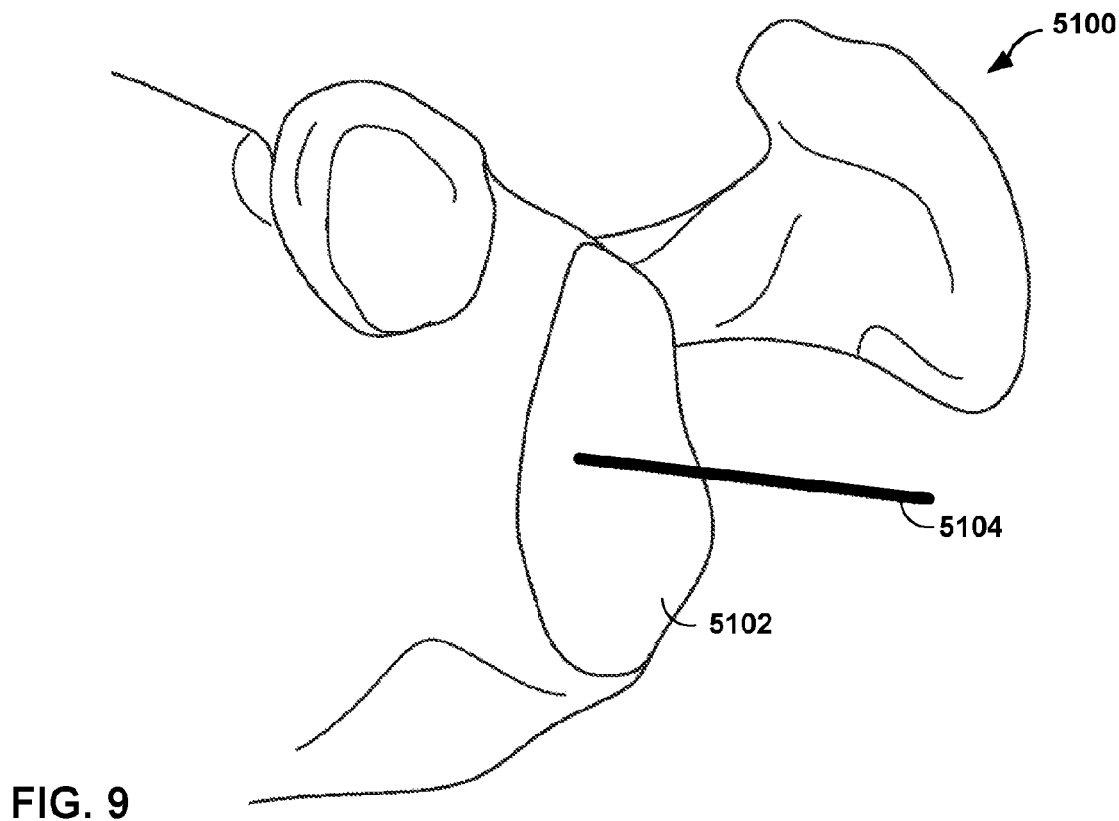
FIGS. 9 and 10 are conceptual diagrams illustrating an MR system providing virtual guidance for installation of a guide pin in a bone, in accordance with one or more techniques of this disclosure.
Figure 10:
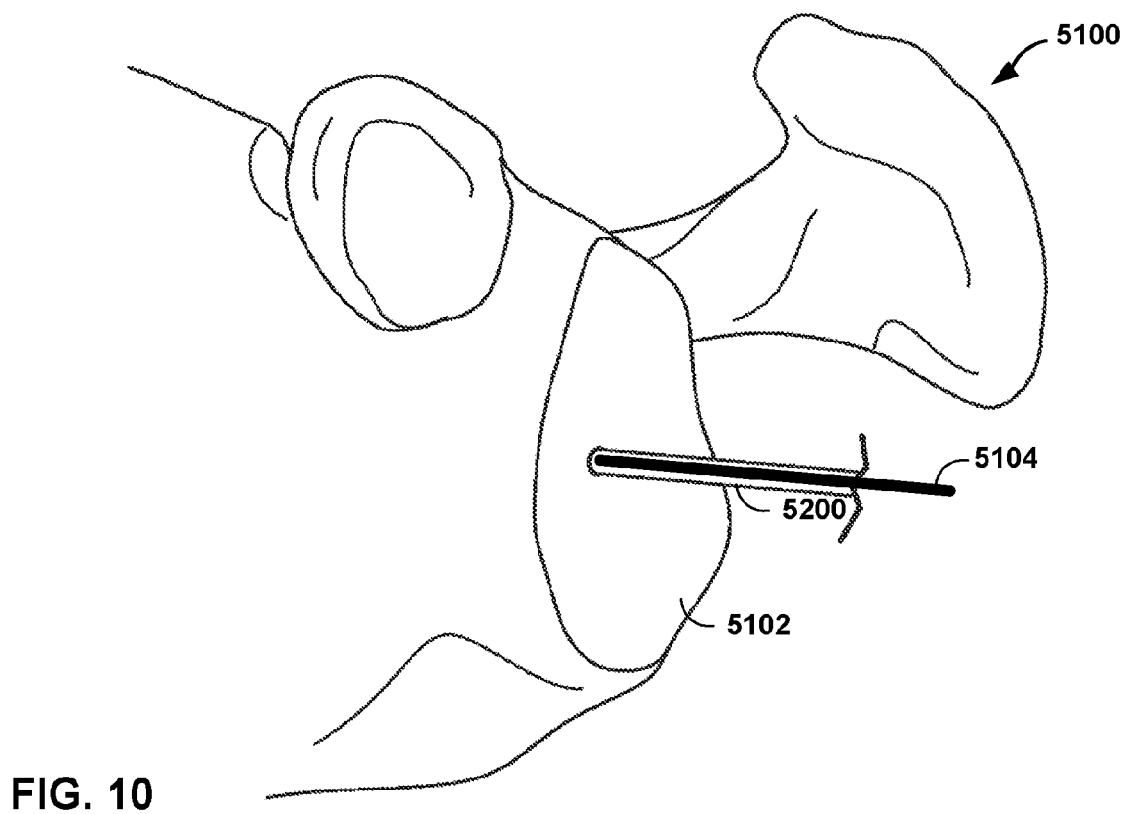

FIGS. 9 and 10 are conceptual diagrams illustrating an MR system providing virtual guidance for installation of a guide pin in a bone, in accordance with one or more techniques of this disclosure. FIGS. 9 and 10 are similar to FIGS. 7 and 8 in that they depict virtual guidance for installation of a guide pin in a bone. However, where FIGS. 7 and 8 depict virtual guidance for installation of a guide pin in a humerus, FIGS. 9 and 10 depict virtual guidance for installation of a guide pin in a scapula. In particular, as shown in FIG. 9, MR system 212 may display virtual guidance, e.g., in the form of virtual axis 5104, on glenoid 5102 of scapula 5100. To display virtual axis 5104, MR system 212 may determine a location on a virtual model of glenoid 5102 at which a guide is to be installed. MR system 212 may obtain the location from a virtual surgical plan (e.g., the virtual surgical plan described above). The location obtained by MR system 212 may specify one or both of coordinates of a point on the virtual model and a vector (e.g., a planned position and a planned orientation). The point may be the position at which the guide is to be installed (e.g., the planned position) and the vector may indicate the angle/slope at which the guide is to be installed (e.g., the planned orientation). As such, MR system 212 may display a virtual reaming axis having parameters (e.g., position, size, and/or orientation relative to the virtual model of the scapula) obtained from the virtual surgical plan. The displayed virtual reaming axis may be configured to guide reaming of the glenoid.

The surgeon may attach a physical guide using the displayed virtual guidance. As one example, where the guide is a guide pin with a self-tapping threaded distal tip, the surgeon may align the guide pin with the displayed virtual axis 5104 and utilize a drill or other instrument to install the guide pin. As another example, where the guide is a guide pin without a self-tapping tip, the surgeon may align a drill bit of a drill with the displayed virtual axis 5104 and operate the drill to form a hole to receive the guide pin and then install the guide pin in the hole. In some examples, MR system 212 may display depth guidance information to enable the surgeon to install the guide pin to a planned depth.

FIG. 10 is a conceptual diagram illustrating guide 5200, i.e., a guide pin in this example, as installed in glenoid 5102. As shown in FIGS. 9 and 10, by displaying virtual axis 5104, a surgeon may drill in alignment with the virtual axis, which may be referred to as a reaming axis, and thereby form a hole for installation of guide 5200 at the planned position on glenoid 5102. In this way, MR system 212 may enable the installation of a guide without the need for an additional mechanical guide.

As discussed above, in some examples, the surgeon may not install a surgical pin (e.g., a guide pin) correctly. For instance, the surgeon may install guide pin 5200 in glenoid 5102 at an incorrect orientation. In some examples, the surgeon may install guide pin 5200 at an incorrect orientation because the virtual axis may be at least partially occluded by the drill, therefore making it difficult to maintain alignment between guide pin 5200 and the virtual axis.

Figure 11:
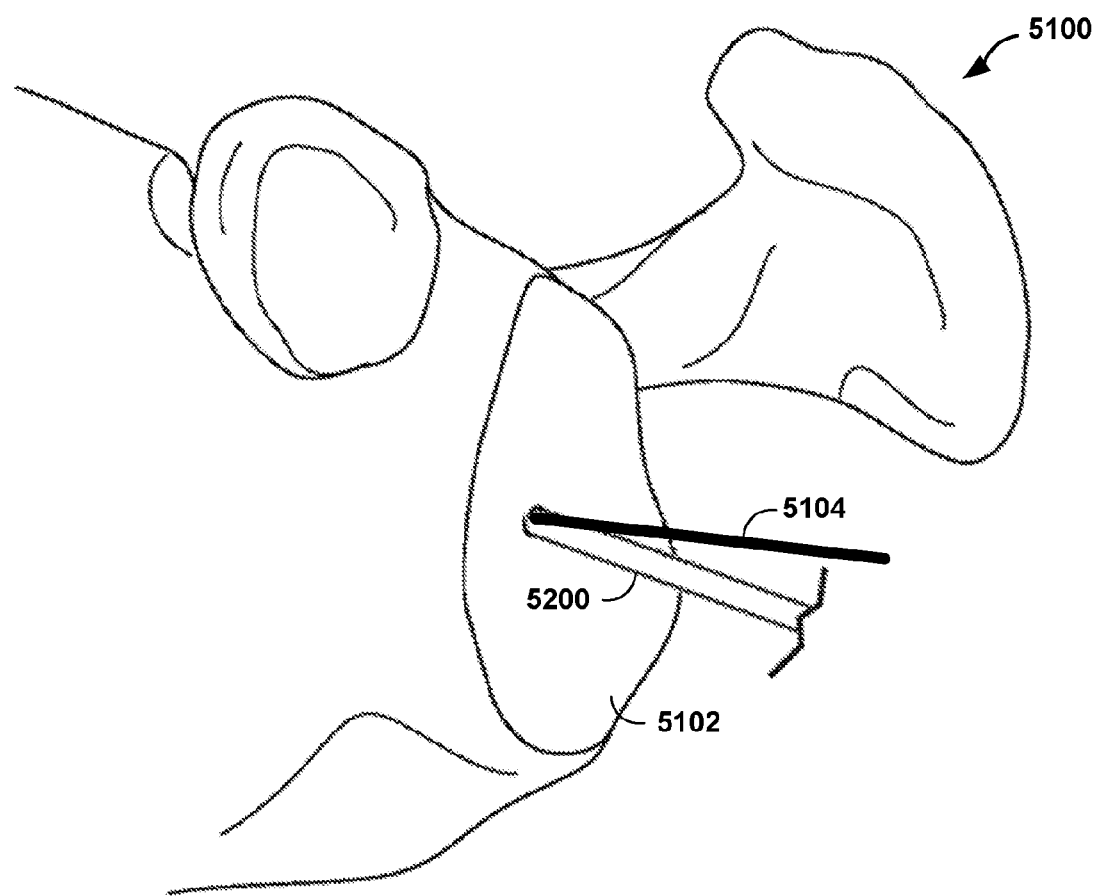
FIG. 11 is a conceptual diagram illustrating a pin installed at an incorrect orientation.

FIG. 11 is a conceptual diagram illustrating a pin installed at an incorrect orientation. As shown in FIG. 11, guide 5200 is actually installed in glenoid 5102 at an orientation that is different than a planned orientation. In particular, while FIG. 11 illustrates guide 5200 installed at the correct location on glenoid 5102, the actual orientation of guide 5200 is approximately 15 degrees off from the planned orientation denoted by virtual axis 5104.

In accordance with one or more techniques of this disclosure, MR system 212 may automatically determine whether a surgical pin was installed correctly. For instance, after initial installation of a surgical pin (e.g., guide 5200) into a bone of a patient (e.g., glenoid 5102), MR system 212 may determine whether an actual orientation of the surgical pin (e.g., as installed) matches a planned orientation of the surgical pin. Further details of how MR system 212 may determine whether the actual orientation matches the planned orientation are described below. Additionally or alternatively, the surgeon may visually determine whether the actual orientation of the surgical pin matches the planned orientation and provide user input (e.g., push a button, provide a verbal command, etc.) to MR system 212 indicating whether the actual orientation of the surgical pin matches the planned orientation.

If the actual orientation does match the planned orientation, MR system 212 may proceed to provide guidance for subsequent steps of the surgical procedure. For instance, MR system 212 may provide guidance to utilize a cannulated tool that is guided by the surgical pin.

If the actual orientation does not match the planned orientation, MR system 212 may output However, in some examples, MR system 212 may provide virtual guidance to assist the surgeon in correcting the installation of a surgical pin (e.g., with or without also providing an output indicating that the actual orientation does not match the planned orientation). In both examples, the surgeon may correct the installation of the surgical pin via any sufficient technique. For instance, the surgeon may correct the orientation of the surgical pin by utilizing bending pliers to physically bend the material of the surgical pin.

Figure 12A:
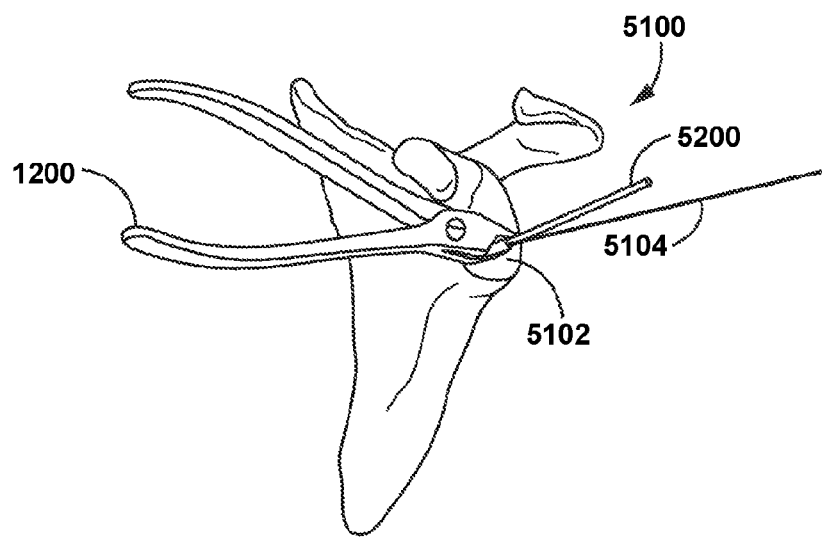
FIGS. 12A-12E are conceptual diagrams of virtual guidance that may be displayed to assist a surgeon in correcting installation of a surgical pin, in accordance with one or more techniques of this disclosure.
Figure 12B:
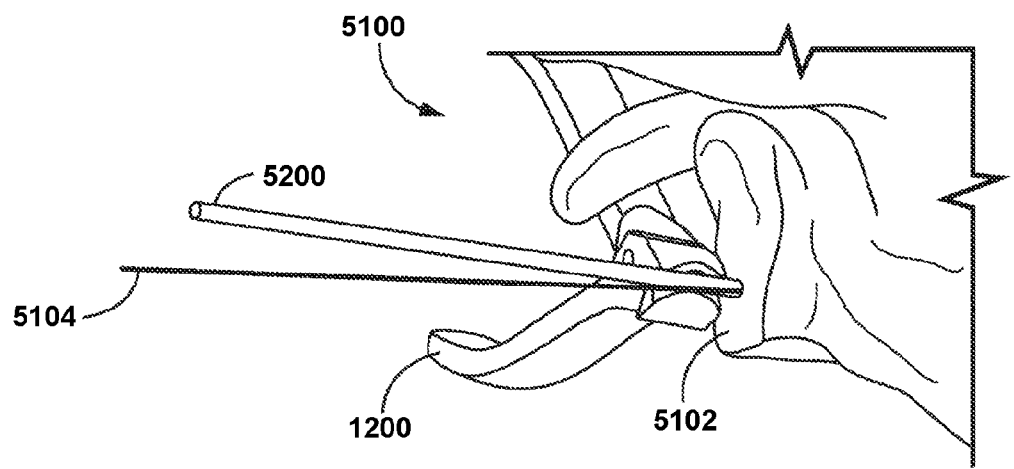

FIGS. 12A-12E are conceptual diagrams of virtual guidance that may be displayed to assist a surgeon in correcting installation of a surgical pin, in accordance with one or more techniques of this disclosure. As shown in FIG. 12A, to output the virtual guidance to assist the surgeon in correcting the installation of guide 5200, MR system 212 may display virtual axis 5104 (i.e., a virtual axis corresponding to the planned orientation). The surgeon may utilize the displayed virtual guidance to correct the orientation of guide 5200. For instance, as shown in FIG. 12A, the surgeon may place bending pliers 1200 (or any other suitable tool) at a base of guide 5200. As shown in FIG. 12B, the surgeon may then align a bending axis of bending pliers 1200 with a desired plane of bending. For instance, the surgeon may rotate bending pliers 1200 such that activation of bending pliers 1200 will result in guide 5200 being bent toward the planned orientation (e.g., the orientation of virtual axis 5104).

Figure 12C:
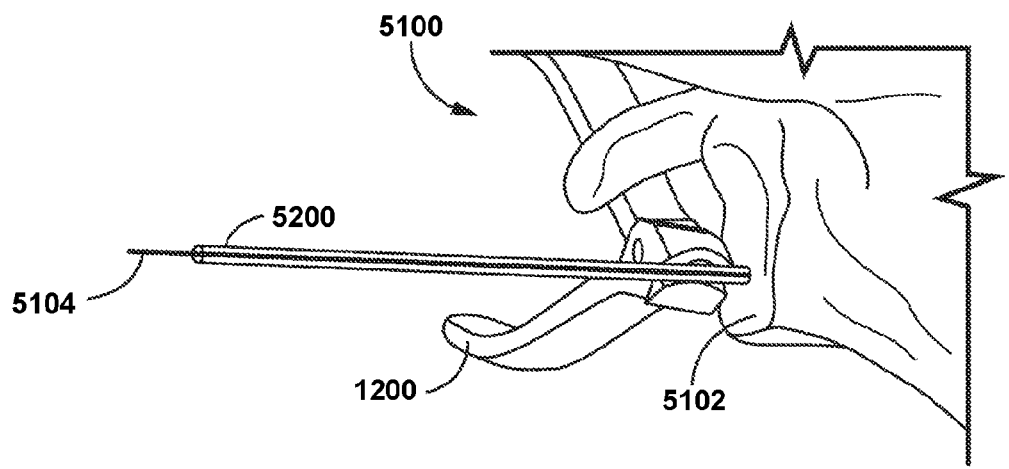
Figure 12D:
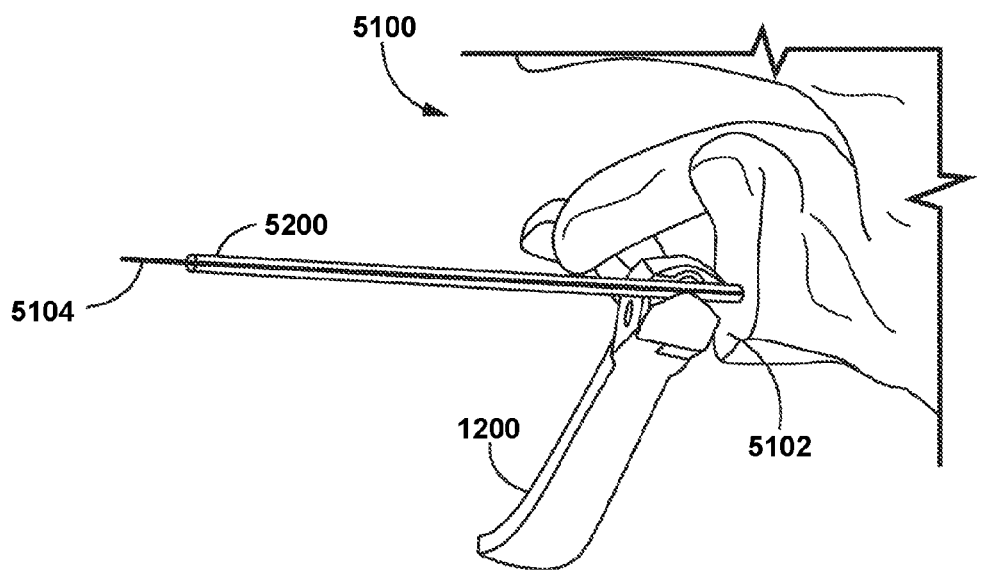
Figure 12E:
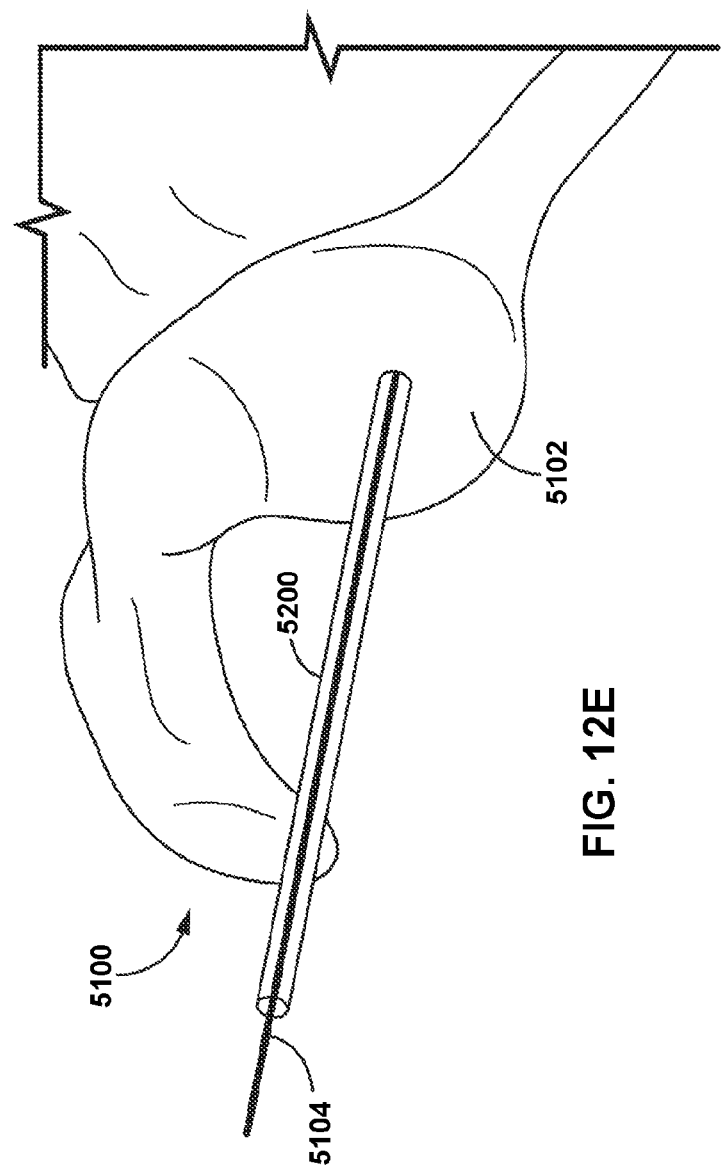

As shown in FIG. 12C, the surgeon may then activate bending pliers 1200 (e.g., squeeze handles of bending pliers 1200) to bend guide 5200 towards the planned orientation. As shown in FIG. 12D, the surgeon may continue to use bending pliers 1200 until guide 5200 reaches the planned orientation. With guide 5200 bent to the planned orientation, the surgeon may remove bending pliers 1200. As shown in FIG. 12E, after bending, the actual orientation of guide 5200 corresponds to the planned orientation. As also shown in FIG. 12E the bending may result in a crease or other deformation in the shape of guide 5200 (e.g., there will be a bend in guide 5200 at the point of bending). In this way, MR system 212 may guide a surgeon in correcting installation of a guide pin.

In some examples, MR system 212 may periodically determine whether a surgical pin (e.g., guide 5200) was installed as planned. Where MR system 212 determines that the surgical pin was not originally installed correctly (e.g., determines that the surgical pin was not installed as planned at a first time), MR system 212 may provide virtual guidance to assist the surgeon in correcting the installation as discussed above and may periodically determine whether installation of the surgical pin has been corrected. For instance, as the surgeon performs steps to correct installation of the surgical pin, MR system 212 may periodically determine a current actual orientation of the surgical pin and compare the determined current actual orientation with the planned orientation to determine whether installation of the guide pin has been corrected.

MR system 212 may determine that installation of the guide pin has been corrected in response to determining that the current actual orientation of the surgical pin matches the planned orientation (e.g., is within a tolerable range, where exact match may be possible but is not necessary). Responsive to determining that installation of the surgical pin has been corrected (e.g., responsive to determining that the surgical pin is installed as planned at a second time that is after the first time), MR system 212 may output an indication that the surgical pin is now installed correctly. MR system 212 may output the indication using any suitable channel. For instance, MR system 212 may output any combination of visual, audible, or haptic indications that the surgical pin is now installed correctly. As one example, where the virtual guidance to assist the surgeon in correcting the installation of the surgical pin includes a virtual axis corresponding to the planned orientation, MR system 212 may adjust a visual characteristic of the displayed virtual axis (e.g., change a color, such as turning from red to green) responsive to determining that installation of the surgical pin has been corrected. As another example, responsive to determining that installation of the surgical pin has been corrected, MR system 212 may display text (e.g., cause visualization device 213 to display text) indicating that installation of the surgical pin has been corrected.

While described above as displaying a virtual axis, MR system 212 may display any variety of virtual guidance elements to assist the surgeon in correcting the installation of the surgical pin. Example virtual guidance elements include, but are not limited to, virtual points, virtual axes, virtual angles, virtual paths, virtual planes, virtual reticles, and virtual surfaces or contours. As one example, the virtual guidance elements to assist the surgeon in correcting the installation of the surgical pin may include a virtual axis corresponding to the actual orientation of the surgical pin. For instance, MR system 212 may display the virtual axis corresponding to the actual orientation of the surgical pin and an animation of the virtual axis corresponding to the actual orientation of the surgical pin moving to the planned orientation (e.g., an animation of the surgical pin moving from the actual orientation to the planned orientation).

While described above as being used to diagnose and correct the installation of a surgical pin in a glenoid of a scapula, the techniques of this disclosure are equally applicable to diagnosing and correcting the installation of surgical pins in any anatomy of a patient. For instance, the techniques of this disclosure may be used to diagnose and correct the installation of a surgical pin in a scapula, a humerus, a tibia, and/or a talus.

In any case, once the installation of the surgical pin has been corrected, the surgeon may continue with the surgical procedure. For instance, the surgeon may utilize the guide pin to guide use of one or more cannulated tools.

Figure 13:
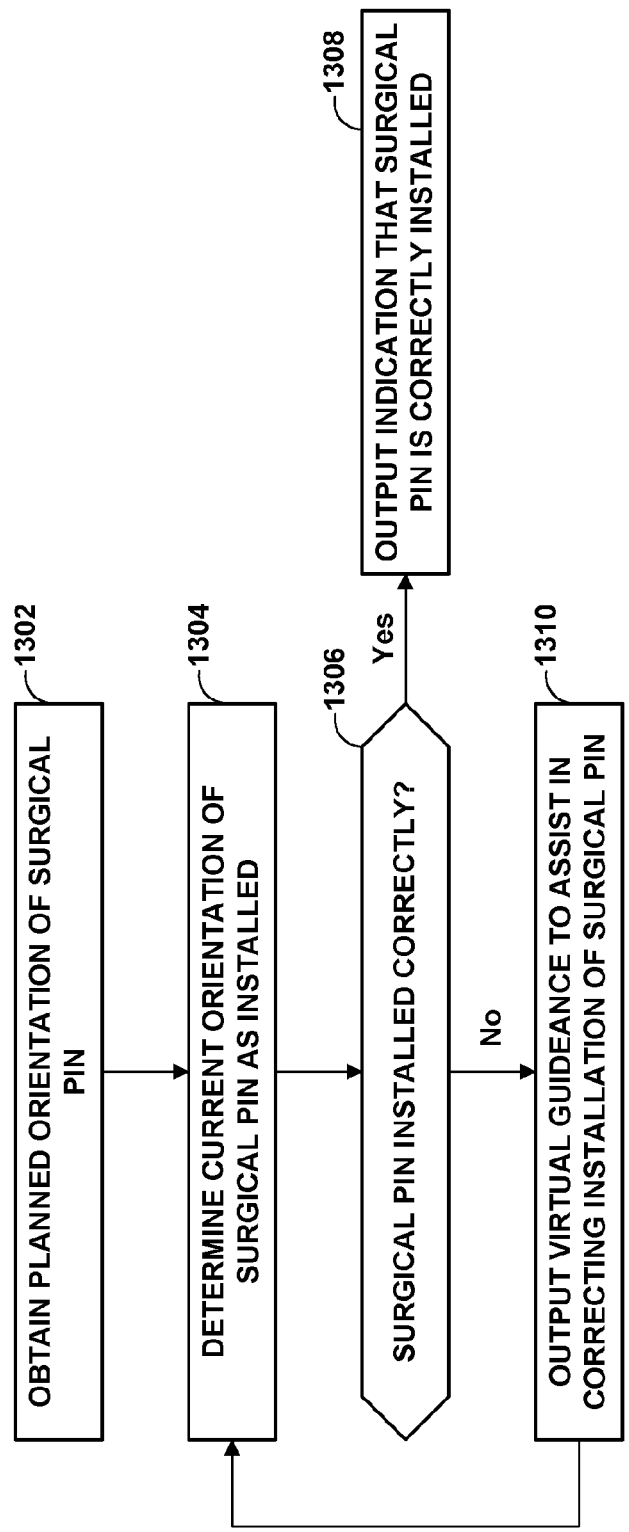
FIG. 13 is a flowchart illustrating example techniques for diagnosing and correcting the installation of surgical pins, in accordance with one or more techniques of this disclosure.

FIG. 13 is a flowchart illustrating example techniques for diagnosing and correcting the installation of surgical pins, in accordance with one or more techniques of this disclosure. For purposes of explanation, the techniques of FIG. 13 are described as being performed by MR system 212 of FIG. 1. However, other mixed-reality systems may perform the techniques of FIG. 13.

MR system 212 may obtain a planned orientation of a surgical pin (1302). For instance, MR system 212 may obtain, from a virtual surgical plan (e.g., the virtual surgical plan described above), a vector indicating an angle/slope at which the surgical is to be installed (e.g., the planned orientation). The vector may be obtained as relative to a virtual model of an anatomy in-which the surgical pin is to be installed. For instance, in the example of FIG. 10, MR system 212 may obtain the planned orientation guide 5200 relative to a virtual model of glenoid 5102.

MR system 212 may determine an actual orientation of the surgical pin (1304). For instance, MR system 212 may process data obtained via one or more sensors of visualization device 213 to determine the actual orientation of the surgical pin.

MR system 212 may determine whether the surgical pin is installed correctly (1306). For instance, MR system 212 may compare the actual orientation of the surgical pin with the planned orientation of the surgical pin. If a difference between the actual orientation and the planned orientation is greater than a threshold difference (e.g., 2 degrees, 5 degrees, 10 degrees, etc.), MR system 212 may determine that the surgical pin is not installed correctly. If the difference between the actual orientation and the planned orientation is not greater than the threshold difference, MR system 212 may determine that the surgical pin is installed correctly.

Responsive to determining that the surgical pin was installed correctly, MR system 212 may output an indication that the surgical pin was installed correctly ("Yes" branch of 1306, 1308). For instance, visualization device 213 may display text indicating that the surgical pin is installed correctly.

Responsive to determining that the surgical pin was not installed correctly, MR system 212 may output virtual guidance to assist in correcting installation of the surgical pin ("No" branch of 1306, 1310). For instance, visualization device 213 may output any of the virtual guidance discussed above with reference to FIGS. 12A-12E.

MR system 212 may update the determination of the current orientation of the surgical pin (1304), and determine whether installation of the surgical pin has been corrected based on the updated current orientation (1306). In this way, MR system 212 may diagnose and correct the installation of a surgical pin.

As discussed above, in some examples, it may be desirable to determine a position and/or an orientation of a surgical pin. For instance, when determining whether a surgical pin was installed correctly, it may be desirable for MR system 212 may be able to determine the position and/or orientation of the surgical pin. In some scenarios, it may be difficult for MR system 212 to be able to determine the actual orientation and/or position of a traditional surgical pin. For instance, where visualization device 213 of MR system 212 is worn on a head of the surgeon who is looking down at a surgical field, it may be difficult for MR system 212 to determine the orientation of a surgical pin in the surgical field.

In accordance with one or more techniques of this disclosure, a surgical pin may include one or more visually marked regions configured to facilitate detection of the surgical pin. For instance, a surgical pin may include two etched or otherwise visually differentiated regions along a shaft. MR system 212 may utilize the visually marked regions of the surgical pin to determine an orientation and/or a position of the surgical pin. For instance, visualization device 213 may utilize one or more cameras to capture an image of the surgical field that includes the surgical pin. MR system 212 may analyze the image to identify end points of each of the one or more visually marked regions, and determine a three-dimensional (3D) location of each end point. Based on the 3D locations of the end points, MR system 212 may determine the orientation and/or the position of the surgical pin.

Figure 14:
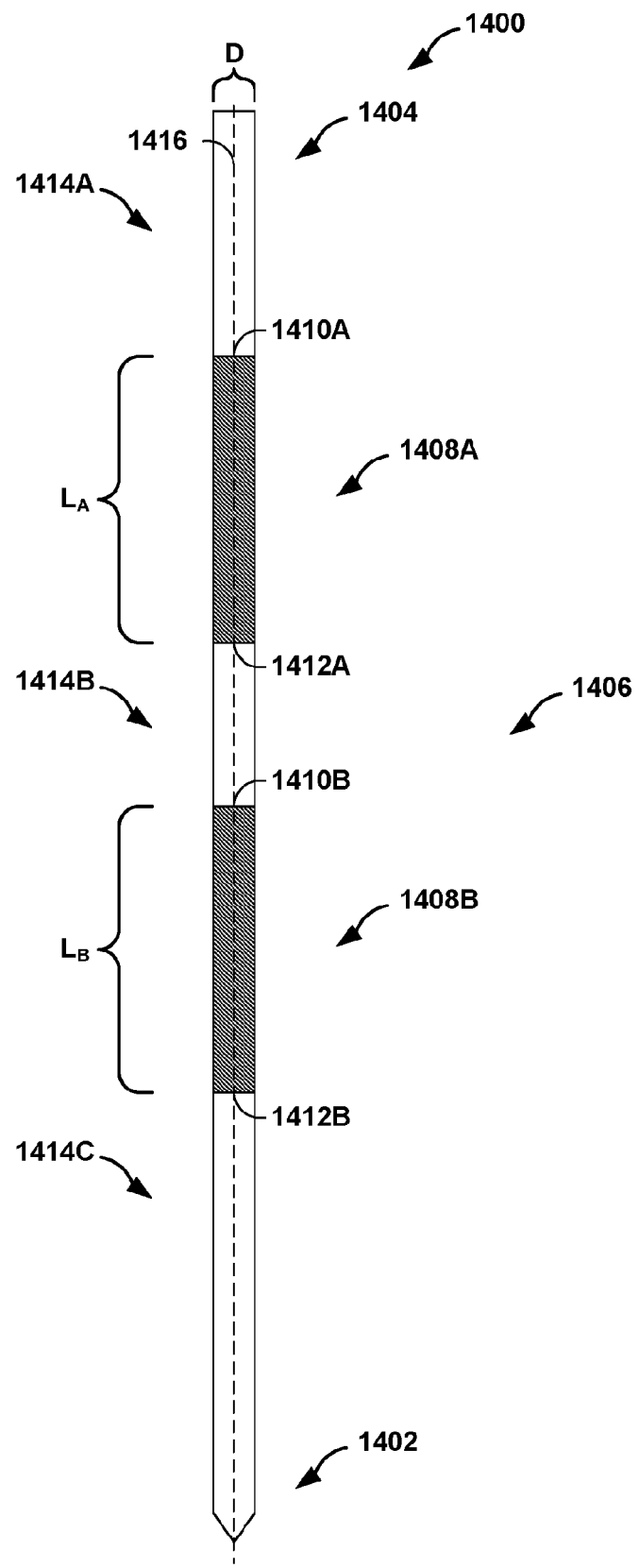
FIG. 14 is a conceptual diagram of surgical pin 1400 that includes one or more visually marked regions configured to facilitate detection of the surgical pin, in accordance with one or more techniques of this disclosure.

FIG. 14 is a conceptual diagram of surgical pin 1400 that includes one or more visually marked regions configured to facilitate detection of the surgical pin, in accordance with one or more techniques of this disclosure. Surgical pin 1400 may be considered to be an example of guide 3500 of FIG. 8, or guide 5200 of FIGS. 10, 11, and 12A-12E. Examples of surgical pin 1400 include, but are not necessarily limited to, Steinmann pins and k-wires.

As shown in FIG. 14, surgical pin 1400 includes shaft 1406 having distal end 1402 and proximal end 1404. Distal end 1402 may be configured to drill into material. For instance, distal end 1402 may have a trocar shape suitable for drilling into bone. Proximal end 1404 may be configured to be attached to a chuck (e.g., of a surgical motor) for transferring rotational energy to surgical pin 1400.

As discussed above, a surgical pin may include one or more visually marked regions configured to facilitate detection of the surgical pin. As shown in FIG. 14, surgical pin 1400 may include visually marked regions 1408A and 1408B (collectively, "visually marked regions 1408"). Visually marked regions 1408 may be longitudinally spaced along longitudinal axis 1416 of surgical pin 1400. For instance, visually marked region 1408A is shown as being longitudinally displaced from (i.e., at a different position along longitudinal axis 1416 than) visually marked region 1408B. Visually marked regions 1408 may have equal longitudinal length or may have different longitudinal length. As one example, the longitudinal length of visually marked region 1408A $L_A$ may be the same as the longitudinal length of visually marked region 1408B $L_B$. As another example, the longitudinal length of visually marked region 1408A $L_A$ may be different than the longitudinal length of visually marked region 1408B $L_B$. Visually marked regions 1408 may be in the shape of bands or rings. In any case, visualization device 213 may store (e.g., in memory) values representing the longitudinal lengths of visually marked regions 1408.

Visually marked regions 1408 may be interspersed/separated by non-marked regions 1414A-1414C (collectively, "non-marked regions 1414"). As shown in the example of FIG. 14, the marked and non-marked regions may be as follows, from proximal end 1404 to distal end 1402, non-marked region 1414A, marked region 1408A, non-marked region 1414B, marked region 1408B, and non-marked region 1414C.

The boundary between a visually marked region and a non-marked region may define a point, which may be referred to as an end point of a visually marked region. For instance, the boundary between non-marked region 1414A and visually marked region 1408A may define endpoint 1410A, the boundary between visually marked region 1408A and non-marked region 1414B may define endpoint 1412A, the boundary between non-marked region 1414B and visually marked region 1408B may define endpoint 1410B, the boundary between visually marked region 1408B and non-marked region 1414C may define endpoint 1412B.

Visually marked regions 1408 may be fabricated to be visually distinct from non-marked regions 1414. As one example, visually marked regions 1408 may have a different color than non-marked regions 1414. For instance, visually marked regions 1408 may be black or dark-gray while non-marked regions 1414 are light gray or white (e.g., metallic color). As another example, visually marked regions 1408 may be fabricated to have a high contrast relative to non-marked regions 1414. For instance, visually marked regions 1408 may be fabricated to be darker than non-marked regions 1414.

Visually marked regions 1408 may be fabricated using any suitable process. As one example, visually marked regions 1408 may be fabricated via etching (e.g., laser etching) surgical pin 1400. As another example, visually marked regions 1408 may be fabricated by applying paint or dye to surgical pin 1400. Visually marked regions 1408 may be fabricated such that surgical pin 1400 may be sterilized (e.g., placed in an autoclave) without visually marked regions 1408 incurring damage.

In addition to being visually distinct from non-marked regions, various aspects of visually marked regions 1408 may be selected to facilitate the detection of surgical pin 1400. As one example, the longitudinal lengths of visually marked regions 1408 may be selected to facilitate the detection of surgical pin 1400. For instance, to increase the visual signal provided by the locations of the end points of visually marked regions 1408 (i.e., endpoints 1410 and 1412), the longitudinal lengths of visually marked regions 1408 may be selected to be significantly larger than a diameter D of surgical pin 1400. For example, $L_A$ and $L_B$ may be selected to be at least five times D. As one specific example, where D is 2.5 mm, $L_A$ and $L_B$ may be selected to be 40 mm.

Figure 15:
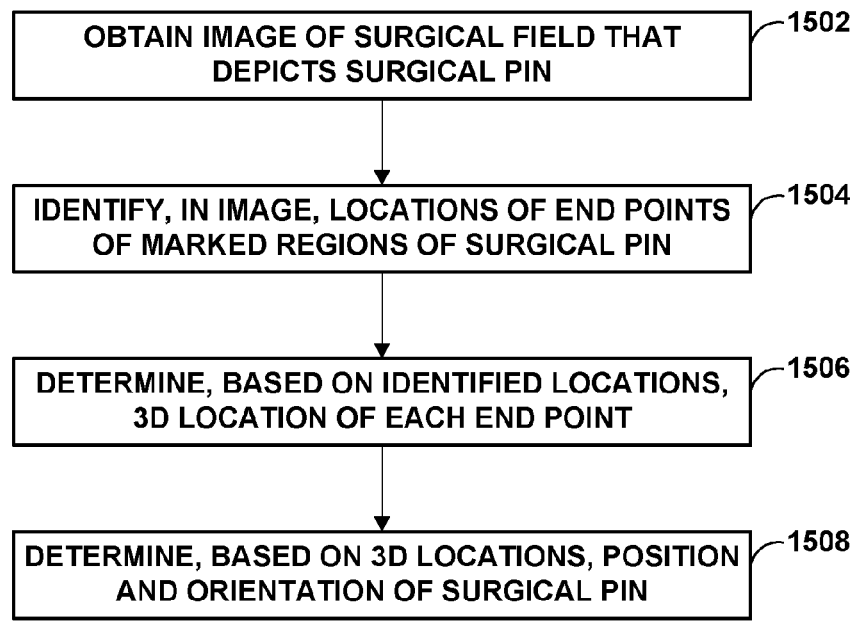
FIG. 15 is a flowchart illustrating example techniques for tracking the position and/or orientation of a surgical pin, in accordance with one or more techniques of this disclosure.

FIG. 15 is a flowchart illustrating example techniques for tracking the position and/or orientation of a surgical pin, in accordance with one or more techniques of this disclosure. For purposes of explanation, the techniques of FIG. 15 are described as being performed by MR system 212 of FIG. 1. However, other mixed-reality systems may perform the techniques of FIG. 15.

MR system 212 may obtain an image of a surgical field that depicts a surgical pin (1502). For instance, one or more cameras of visualization device 213 may capture an image that includes surgical pin 1400 of FIG. 14, which includes one or more longitudinally spaced visually marked regions. As one example, one or more RGB cameras of visualization device 213 may capture the image (e.g., a texture image of the surgical field). As another example, one or more depth cameras of visualization device 213 may capture the image (e.g., may capture a depth map of the surgical field).

MR system 212 may identify, in the image, locations of end points of each of the one or more marked regions (1504). For instance, processors 210 of MR system 212 may process the image (e.g., using thresholding or any other boundary detection algorithm) to identify locations of end points 1410A, 1412A, 1410B, and 1412B of surgical pin 1400 in the image. The identification of the end points in the image may be in the form of which pixels or samples in the image correspond to the end points.

MR system 212 may determine, based on the identified locations of the end points in the image, a respective three-dimensional (3D) location of each respective end points of the end points of the one or more marked regions (1506). For instance, processors 210 may calculate a 3D coordinate (e.g., an x,y,z coordinate set) for each of end points 1410A, 1412A, 1410B, and 1412B of surgical pin 1400. As one example, processors 210 may determine, use a depth camera, depth values for points corresponding to the identified end points of each of the one or more marked regions. As another example, processors 210 may utilize a perspective-n-point algorithm (e.g., where N=2) to determine the 3D locations of the end points.

In some examples, MR system 212 may determine the 3D locations based on one or more pre-determined parameters of the surgical pin. For instance, processors 210 may obtain, from memory 215 of MR system 212, longitudinal lengths of each of the marked regions of the surgical pin (e.g., obtain values for $L_A$ and $L_B$). Processors 210 may determine the respective 3D location of each respective end point based on the longitudinal lengths of each of the marked regions.

In some examples, MR system 212 may determine the 3D locations based on one or more pre-determined parameters of the camera(s) that captured the image. For instance, processors 210 may obtain, from memory 215 of MR system 212, one or more parameters of RGB cameras of visualization device 213. Processors 210 may determine the respective 3D location of each respective end point based on the parameters of the RGB cameras. For instance, processors 10 may transform the respective locations of the end points in the image to the respective 3D locations the end points based on pre-determined characteristics of the RGB cameras.

As discussed above, in some examples, obtained image may be a texture image of the surgical field. In some examples, in addition to the texture image, MR system 212 may obtain a depth map of the surgical field (e.g., as captured by one or more depth cameras of visualization device 213). MR system 212 may, in some examples, determine the 3D locations based on the identified locations of the end point in the image and the depth map. For instance, MR system 212 may map the respective locations of the end points in the texture image to corresponding locations in the depth map (e.g., select a sample in the depth map that corresponds to a sample in the texture image identified as a location of an end point). MR system 212 may determine the respective 3D locations of the end points based on the corresponding locations in the depth map.

MR system 212 may determine, based on the determined 3D locations, a position and/or an orientation of the surgical pin (1508). For instance, processors 210 may generate a vector connecting the 3D locations of the end points, the vector representing the orientation of the surgical pin. Processors 210 may determine the position of the surgical point as a point at which the vector intersects with a virtual model of anatomy registered to a corresponding portion of actual anatomy (e.g., a virtual model of glenoid 5102 that is registered that the patient's actual glenoid).

MR system 212 may utilize the determined position and/or orientation of the surgical pin for any suitable purpose. As one example, MR system 212 may utilize the determined position and/or orientation of the surgical pin to provide virtual guidance. As another example, 212 may utilize the determined position and/or orientation of the surgical pin to determine whether the surgical pin was properly installed (e.g., as discussed above).

The following numbered examples may illustrate one or more aspects of the disclosure:

Example 1. A surgical pin configured to be installed in a bone of a patient, the surgical pin comprising: a distal end; a shaft comprising a plurality of longitudinally spaced visually marked regions separated by non-marked regions; and proximal end.

Example 2. The surgical pin of example 1, wherein each marked region of the plurality of marked regions comprises a band.

Example 3. The surgical pin of example 2, wherein a longitudinal length of a particular band is greater than five times a diameter of the particular band.

Example 4. The surgical pin of any of examples 1-3, wherein the plurality of marked regions are of equal longitudinal length.

Example 5. The surgical pin of any of examples 1-4, wherein a diameter of the marked regions of the shaft is not greater than a diameter of the non-marked regions of the shaft.

Example 6. The surgical pin of example 5, wherein the diameter of the marked regions of the shaft and the diameter of the non-marked regions of the shaft are equal.

Example 7. The surgical pin of example 5, wherein the diameter of the marked regions of the shaft and the diameter of the non-marked regions of the shaft are different.

Example 8. The surgical pin of example 7, wherein the diameter of the marked regions of the shaft is less than the diameter of the non-marked regions of the shaft.

Example 9. The surgical pin of example 8, wherein the diameter of the marked regions of the shaft is 2 millimeters and the diameter of the non-marked regions of the shaft is 2.5 millimeters.

Example 10. The surgical pin of any of examples 1-9, wherein each marked region of the plurality of marked region is etched into the shaft.

Example 11. The surgical pin of any of examples 1-10, wherein the marked regions have a different color than the non-marked regions.

Example 12. The surgical pin of any of examples 1-11, wherein the marked regions are darker than the non-marked regions.

Example 13. The surgical pin of any of examples 1-12, wherein the plurality of marked regions includes exactly two marked regions of equal longitudinal length separated by a single non-marked region.

Example 14. The surgical pin of any of examples 1-13, wherein the surgical pin is configured to undergo sterilization, and wherein the plurality of marked regions are configured to undergo the sterilization without incurring damage to the surgical pin.

Example 15. The surgical pin of any of examples 1-14, wherein the surgical pin is a Steinmann pin.

Example 16. The surgical pin of any of examples 1-15, wherein the distal end is configured to drill into the bone, and wherein the proximal end is configured to be attached to a chuck for rotation.

Example 17. A method comprising: obtaining, via one or more cameras of a visualization device, an image of a surgical field that depicts a surgical pin that includes one or more longitudinally spaced visually marked regions; identifying, by one or more processors and in the image, locations of end points of each of the one or more marked regions; determining, by the one or more processors and based on the identified locations of the end points in the image, a respective three-dimensional (3D) location of each respective end points of the end points of the one or more marked regions; and determining, by the one or more processors and based on the determined 3D locations, a position and an orientation of the surgical pin within the surgical field.

Example 18. The method of example 17, wherein obtaining the image comprises: obtaining, via one or more RGB cameras of the visualization device, the image.

Example 19. The method of example 17 or 18, wherein determining the respective 3D location of each respective end point comprises: obtaining a pre-determined longitudinal length of the one or more marked regions; determining, based on the identified locations of the end points in the image and the longitudinal length of the one or more marked regions, the respective 3D location of each respective end point.

Example 20. The method of any of examples 18 or 19, wherein determining the respective 3D location of each respective end point comprises: transforming, based on pre-determined characteristics of the one or more cameras, the respective locations of the end points in the image to the respective 3D locations the end points.

Example 21. The method of any of examples 17-20, wherein the image comprises a texture image, the method further comprising: obtaining, via one or more depth cameras of the visualization device, a depth map of the surgical field.

Example 22. The method of example 21, wherein determining the respective 3D location of each respective end point comprises: mapping the respective locations of the end points in the texture image to corresponding locations in the depth map; and determining the respective 3D locations of the end points based on the corresponding locations in the depth map.

Example 23. The method of example 17, wherein obtaining the image comprises: obtaining, via one or more depth cameras of the visualization device, the image.

Example 24. The method of any of examples 17-26, further comprising: displaying, via the visualization device and based on one or both of the position and the orientation of the surgical pin, virtual guidance.

Example 25. The method of any of examples 17-27, wherein the image is captured during performance of a surgical procedure.

Example 26. The method of any of examples 17-27, wherein the surgical pin comprises the surgical pin of any of examples 1-16.

Example 27. A system comprising: one or more processors that are implemented in circuitry; and a computer-readable storage medium storing instructions that, when executed, cause the one or more processors to perform the method of any combination of examples 17-26.

Example 28. A computer-readable storage medium storing instructions that, when executed, cause one or more processors to perform the method of any combination of examples 17-26.

Example 29. A method comprising: determining, by the one or more processors, an actual orientation of a surgical pin as installed in a bone of a patient; obtaining, by the one or more processors, a planned orientation of the surgical pin; determining, by the one or more processors and based on a comparison between the actual orientation of the surgical pin and the planned orientation of the surgical pin, whether the surgical pin was installed as planned; and responsive to determining that the surgical pin was not installed as planned, outputting, via a visualization device, virtual guidance to assist a surgeon in correcting the installation of the surgical pin.

Example 30. The method of example 29, wherein outputting the virtual guidance comprises: displaying, via the visualization device, a virtual axis corresponding to the planned orientation.

Example 31. The method of any of examples 29 or 30, wherein determining whether the surgical pin was installed as planned comprises periodically determining whether the surgical pin was installed as planned, determining that the surgical pin was not installed as planned comprises determining that the surgical pin was not installed as planned at a first time, the method further comprising: responsive to determining that the surgical pin is installed as planned at a second time that is after the first time, outputting, via the visualization device, an indication that the surgical pin is installed correctly.

Example 32. The method of example 31, wherein outputting the indication that the surgical pin is installed correctly comprises outputting a visual, audible, or haptic indication that the surgical pin is installed correctly.

Example 33. The method of example 31 or 32, wherein outputting the indication that the surgical pin is installed correctly comprises adjusting a visual characteristic of the displayed virtual axis corresponding to the planned orientation.

Example 34. The method of any of examples 29-33, wherein outputting the virtual guidance comprises: displaying, via the visualization device, a virtual axis corresponding to the actual orientation of the surgical pin.

Example 35. The method of any of examples 29-34, wherein outputting the virtual guidance comprises: displaying, via the visualization device, an animation of the surgical pin moving from the actual orientation to the planned orientation.

Example 36. The method of any of examples 29-35, wherein the bone of the patient comprises a scapula, a humerus, a tibia, and/or a talus.

Example 37. The method of any of examples 29-36, wherein the surgical pin comprises the surgical pin of any of examples 1-16.

Example 38. A system comprising: one or more processors that are implemented in circuitry; and a computer-readable storage medium storing instructions that, when executed, cause the one or more processors to perform the method of any combination of examples 29-37.

Example 39. A computer-readable storage medium storing instructions that, when executed, cause one or more processors to perform the method of any combination of examples 29-37.

Example 40. Any combination of examples 1-39.

While the techniques been disclosed with respect to a limited number of examples, those skilled in the art, having the benefit of this disclosure, will appreciate numerous modifications and variations there from. For instance, it is contemplated that any reasonable combination of the described examples may be performed. It is intended that the appended claims cover such modifications and variations as fall within the true spirit and scope of the invention.

It is to be recognized that depending on the example, certain acts or events of any of the techniques described herein can be performed in a different sequence, may be added, merged, or left out altogether (e.g., not all described acts or events are necessary for the practice of the techniques). Moreover, in certain examples, acts or events may be performed concurrently, e.g., through multi-threaded processing, interrupt processing, or multiple processors, rather than sequentially.

In one or more examples, the functions described may be implemented in hardware, software, firmware, or any combination thereof. If implemented in software, the functions may be stored on or transmitted over as one or more instructions or code on a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transitory media, but are instead directed to non-transitory, tangible storage media. Disk and disc, as used herein, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Operations described in this disclosure may be performed by one or more processors, which may be implemented as fixed-function processing circuits, programmable circuits, or combinations thereof, such as one or more digital signal processors (DSPs), general purpose microprocessors, application specific integrated circuits (ASICs), field programmable gate arrays (FPGAs), or other equivalent integrated or discrete logic circuitry. Fixed-function circuits refer to circuits that provide particular functionality and are preset on the operations that can be performed. Programmable circuits refer to circuits that can programmed to perform various tasks and provide flexible functionality in the operations that can be performed. For instance, programmable circuits may execute instructions specified by software or firmware that cause the programmable circuits to operate in the manner defined by instructions of the software or firmware. Fixed-function circuits may execute software instructions (e.g., to receive parameters or output parameters), but the types of operations that the fixed-function circuits perform are generally immutable. Accordingly, the terms "processor" and "processing circuitry," as used herein may refer to any of the foregoing structures or any other structure suitable for implementation of the techniques described herein.

Various examples have been described. These and other examples are within the scope of the following claims.

What is claimed is:

1. A method comprising:
obtaining, via one or more cameras of a visualization device, an image of a surgical field that depicts a surgical pin that includes one or more longitudinally spaced visually marked regions;
identifying, by one or more processors and in the image, locations of end points of each of the one or more marked regions;
determining, by the one or more processors and based on the identified locations of the end points in the image, a respective three-dimensional (3D) location of each respective end points of the end points of the one or more marked regions; and
determining, by the one or more processors and based on the determined 3D locations, a position and an orientation of the surgical pin within the surgical field.

2. The method of claim 1, wherein obtaining the image comprises:
  obtaining, via one or more RGB cameras of the visualization device, the image.

3. The method of claim 1, wherein determining the respective 3D location of each respective end point comprises:
  obtaining a pre-determined longitudinal length of the one or more marked regions; and
  determining, based on the identified locations of the end points in the image and the longitudinal length of the one or more marked regions, the respective 3D location of each respective end point.

4. A computer-readable storage medium storing instructions that, when executed, cause one or more processors to:
  obtain, via one or more cameras of a visualization device, an image of a surgical field that depicts a surgical pin that includes one or more longitudinally spaced visually marked regions;
  identify, in the image, locations of end points of each of the one or more marked regions;
  determine, based on the identified locations of the end points in the image, a respective three-dimensional (3D) location of each respective end points of the end points of the one or more marked regions; and
  determine, by the one or more processors and based on the determined 3D locations, a position and an orientation of the surgical pin within the surgical field.

* * * * *